US012427206B2

(12) United States Patent
Zuker et al.

(10) Patent No.: US 12,427,206 B2
(45) Date of Patent: Sep. 30, 2025

(54) METHOD OF ASSESSING REGULATION OF AN IMMUNE RESPONSE TO AN ADMINISTERED AGENT BY MEASURING ACTIVATION OF NODOSE GANGLION NEURONS

(71) Applicant: The Trustees of Columbia University in the City of New York, New York, NY (US)

(72) Inventors: Charles S. Zuker, New York, NY (US); Hao Jin, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 18/505,590

(22) Filed: Nov. 9, 2023

(65) Prior Publication Data

US 2024/0075168 A1 Mar. 7, 2024

Related U.S. Application Data

(63) Continuation of application No. PCT/US2022/081626, filed on Dec. 15, 2022.

(60) Provisional application No. 63/289,851, filed on Dec. 15, 2021.

(51) Int. Cl.
*A61K 49/00* (2006.01)
*C07K 14/47* (2006.01)
*G01N 33/50* (2006.01)
*C07K 14/525* (2006.01)
*C07K 14/54* (2006.01)
*C07K 14/545* (2006.01)

(52) U.S. Cl.
CPC ...... *A61K 49/0004* (2013.01); *C07K 14/4728* (2013.01); *G01N 33/5058* (2013.01); *C07K 14/525* (2013.01); *C07K 14/5406* (2013.01); *C07K 14/5412* (2013.01); *C07K 14/5428* (2013.01); *C07K 14/545* (2013.01); *C07K 2319/60* (2013.01); *G01N 2333/4727* (2013.01)

(58) Field of Classification Search
CPC ........... A61K 49/0004; G01N 33/5058; G01N 2333/4727; C07K 14/4728; C07K 14/525; C07K 14/545; C07K 14/5412; C07K 14/4528; C07K 14/5406
See application file for complete search history.

(56) References Cited

U.S. PATENT DOCUMENTS

| 7,769,442 | B2 | 8/2010 | Shafer |
| 8,003,632 | B2 | 8/2011 | Tracey et al. |
| 9,211,409 | B2 | 12/2015 | Tracey et al. |
| 9,592,228 | B2 | 3/2017 | Tracey et al. |
| 10,495,554 | B2 | 12/2019 | Deisseroth et al. |
| 10,507,327 | B2 | 12/2019 | Tracey et al. |
| 2017/0281772 | A1 | 10/2017 | Zuker et al. |
| 2018/0193414 | A1 | 7/2018 | Greenberg et al. |
| 2019/0255175 | A1 | 8/2019 | Tracey et al. |
| 2020/0246329 | A1 | 8/2020 | Rolls et al. |

FOREIGN PATENT DOCUMENTS

| WO | WO 2019/018438 | 1/2019 |
| WO | WO 2019/241795 | 12/2019 |
| WO | WO 2020/239967 | 12/2020 |

OTHER PUBLICATIONS

Makhmutova et al, 2021, Gastroenterology; 160:875-888 and e1-e11 (25 pages total); published on-line Oct. 26, 2020.*
Pavlov et al, 2012. Nat Rev Endocrinol. 8(12): 743-754; pp. 1-30 as printed.*
Jin et al, 2024. Nature. 630: 696-703; 38 pages as printed.*
Borovikova et al., Vagus nerve stimulation attenuates the systemic inflammatory response to endotoxin. Nature. May 25, 2000;405(6785):458-62.
Elmquist et al., Distribution of Fos-like immunoreactivity in the rat brain following intravenous lipopolysaccharide administration. J Comp Neurol. Jul. 15, 1996;371(1):85-103.
Engler et al., Chemical destruction of brain noradrenergic neurons affects splenic cytokine production. J Neuroimmunol. Feb. 26, 2010;219(1-2):75-80.
Guenthner et al., Permanent Genetic Access to Transiently Active Neurons via TRAP: Targeted Recombination in Active Populations. Neuron. Jun. 5, 2013; 78(5): 773-784.
International Search Report and Written Opinion for PCT/US22/81626. Mailed May 26, 2023. 12 pages.
Ji et al., Central cholinergic activation of a vagus nerve-to-spleen circuit alleviates experimental colitis. Mucosal Immunol. Mar. 2014;7(2):335-47.
Nassenstein et al., Expression and function of the ion channel TRPA1 in vagal afferent nerves innervating mouse lungs. J Physiol. Mar. 15, 2008;586(6):1595-604.
Pavlov et al., Brain acetylcholinesterase activity controls systemic cytokine levels through the cholinergic anti-inflammatory pathway. Brain Behav Immun. Jan. 2009; 23(1): 41-45.
Pavlov et al., Selective alpha7-nicotinic acetylcholine receptor agonist GTS-21 improves survival in murine endotoxemia and severe sepsis. Crit Care Med. Apr. 2007;35(4):1139-44.

(Continued)

*Primary Examiner* — Zachary C Howard
(74) *Attorney, Agent, or Firm* — Casimir Jones, S.C.; Kelly A. Barton

(57) ABSTRACT

Disclosed herein are methods for regulating an immune response using selective activation of neurons in the caudal nucleus of the solitary tract.

15 Claims, 25 Drawing Sheets

(56) References Cited

OTHER PUBLICATIONS

Ramirez et al., Neural Immune Communication in the Control of Host-Bacterial Pathogen Interactions in the Gastrointestinal Tract. Infect Immun. Aug. 19, 2020;88(9):e00928-19.

Rosas-Ballina et al., Xanomeline suppresses excessive pro-inflammatory cytokine responses through neural signal-mediated pathways and improves survival in lethal inflammation. Brain Behav Immun. Feb. 2015:44:19-27.

Sundman et al., Neural control of the immune system. Adv Physiol Educ. Jun. 2014;38(2):135-9.

Tarkowski et al., Enhancement of antigen-specific T-cell reactivity on the affected side in stroke patients. J Neuroimmunol. Oct. 1991;34(1):61-7.

* cited by examiner

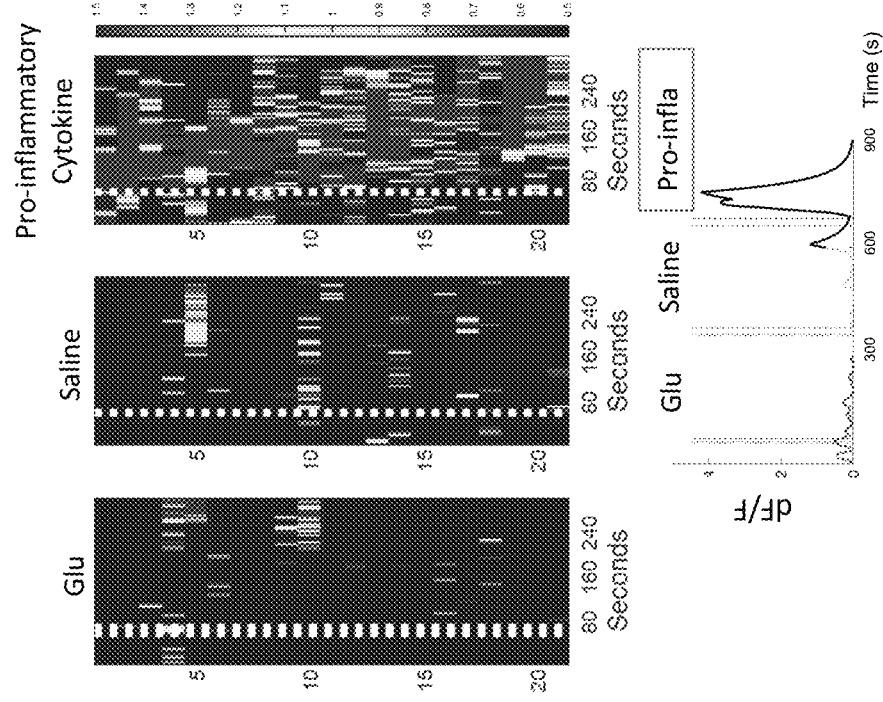
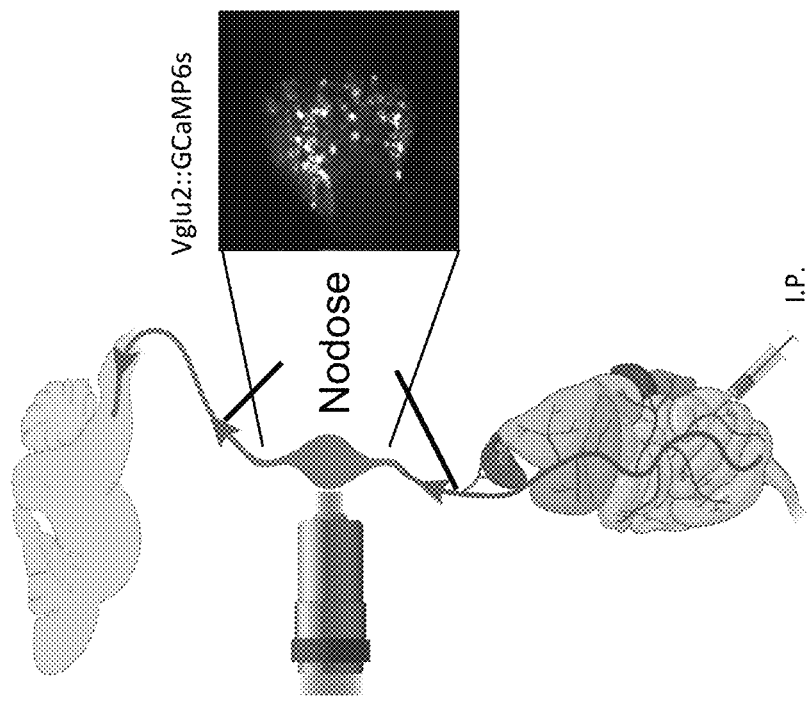
FIG. 7

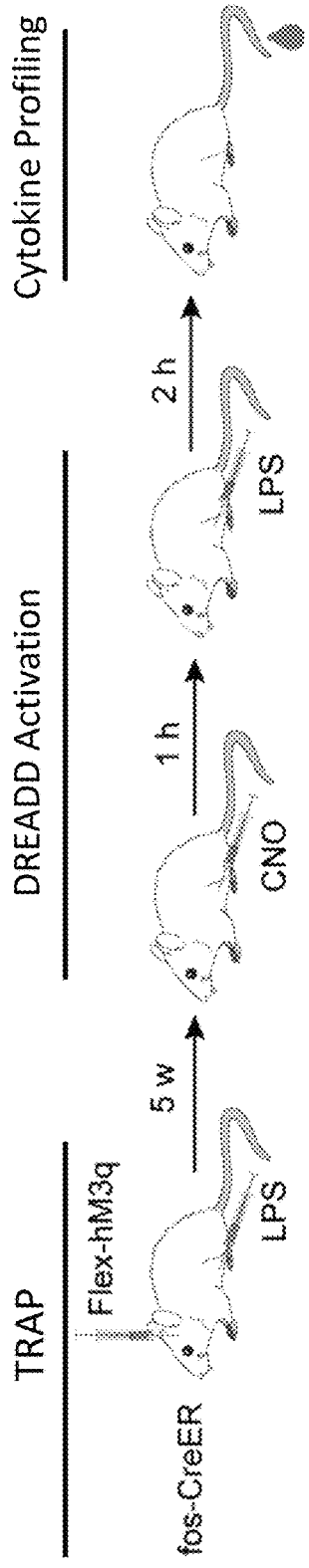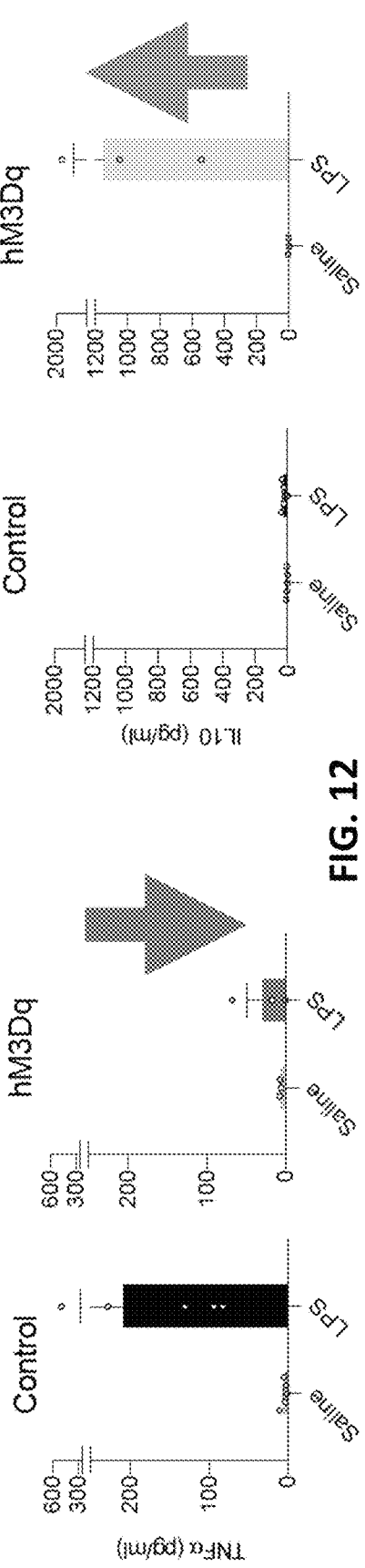
FIG. 12

The brain uses neural circuits to modulate immune responses in the body.

Neural and Immunological basis of learned immune modulation a) Immune signals function as the unconditioned stimulus
b) The olfactory cue is endowed with the immune modulating capacity through associative learning

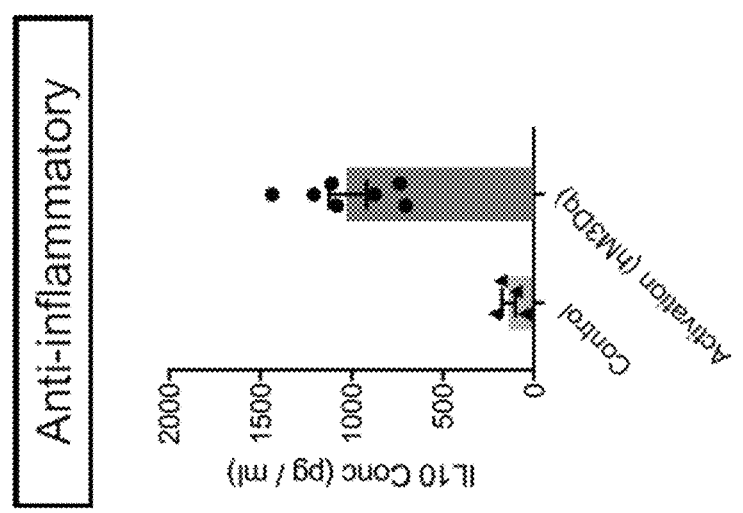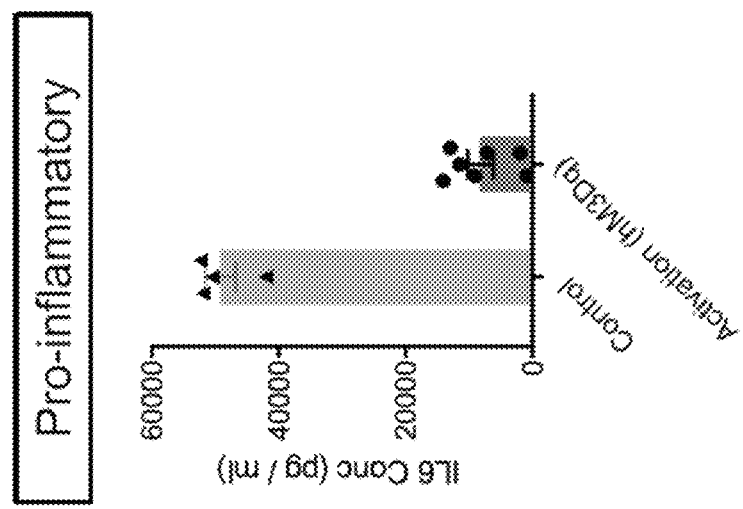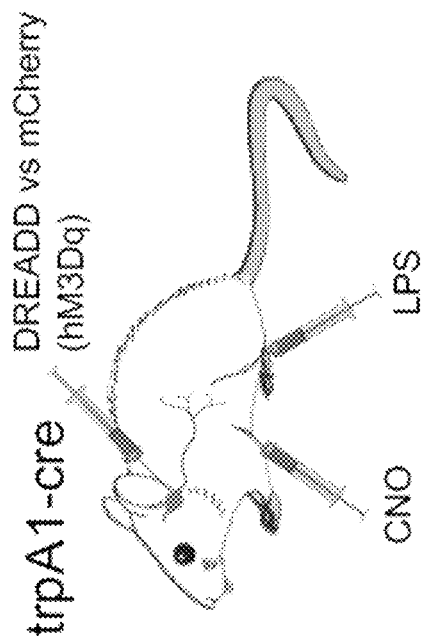
FIG. 22

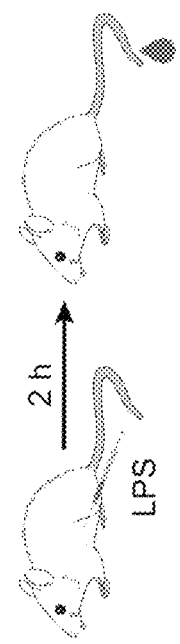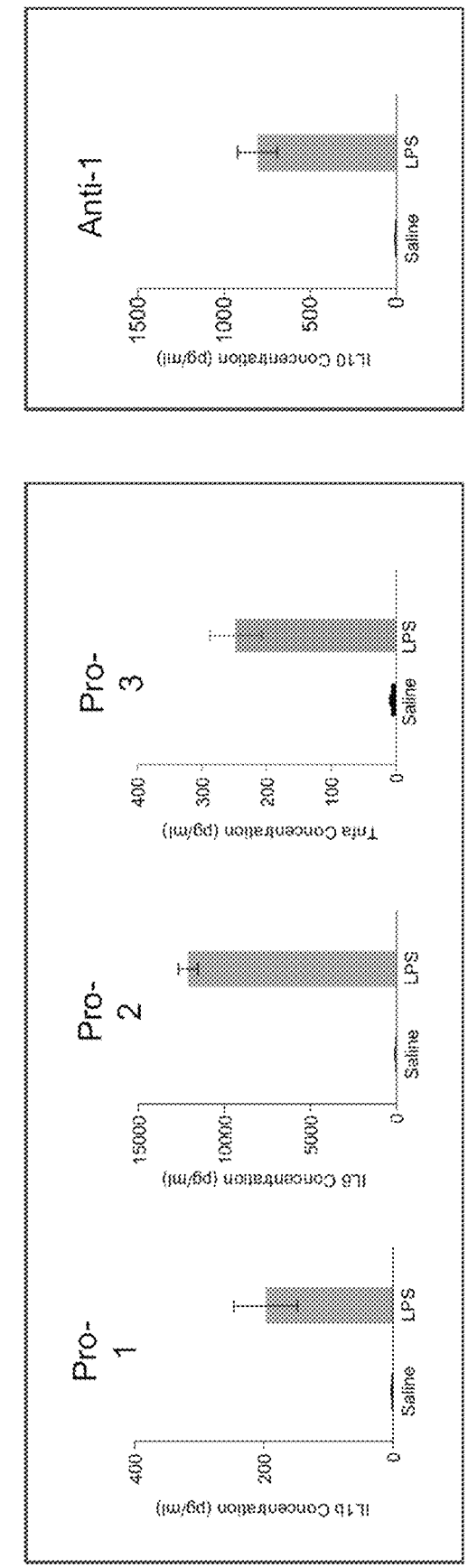
FIG. 24

METHOD OF ASSESSING REGULATION OF AN IMMUNE RESPONSE TO AN ADMINISTERED AGENT BY MEASURING ACTIVATION OF NODOSE GANGLION NEURONS

CROSS-REFERENCE TO RELATED APPLICATIONS

This application is a continuation of International Application Serial Number PCT/US2022/081626, filed on Dec. 15, 2022, which claims priority to U.S. Provisional Application Ser. No. 63/289,851, filed on Dec. 15, 2021, the disclosures of which are hereby incorporated by reference in its entirety.

TECHNICAL FIELD

Disclosed herein are methods of regulating the immune response.

BACKGROUND OF THE INVENTION

Immune responses play critical roles in the body's ability to maintain health and fight disease. Anatomically, there are extensive bidirectional connections between the brain and the immune system suggesting that the brain could monitor and modulate peripherical immune activity. However, the functional meaning of these connections in the neuronal control of immune response remains largely unknown. Regulation of the immune response is a central strategy to treat disease and injury making novel methods to control the immune response essential to the advancement of health and medicine.

SUMMARY OF THE INVENTION

Disclosed herein are methods of regulating an immune response in a mammal comprising modulating the activity of one or more TRPA1-expressing neurons in a vagal ganglion of the mammal to thereby regulate the immune response, wherein, when the neuron is engineered to express a designer receptor exclusively activated by a designer drug (DREADD), there is a decreased serum level of one or more proinflammatory cytokines and/or an increased serum level of one or more anti-inflammatory cytokines in the presence of a DREADD ligand.

Disclosed herein are methods of regulating an immune response in a mammal comprising modulating the activity of one or more CGRP receptor-expressing neurons in a vagal ganglion of the mammal to thereby regulate the immune response, wherein, when the neuron is engineered to express a DREADD, there is an increased serum level of one or more proinflammatory cytokines and/or a decreased serum level of one or more anti-inflammatory cytokines in the presence of a DREADD ligand.

Disclosed herein are methods of regulating an immune response in a mammal comprising modulating the activity of one or more neurons in the brainstem of the mammal, wherein, the neuron is activated by lipopolysaccharide (LPS) to induce release of pro-inflammatory cytokines, and wherein, when the neuron is engineered to express a DREADD, there is a reduced LPS-evoked release of pro-inflammatory cytokines and/or increased release of anti-inflammatory cytokines in the presence of a DREADD ligand.

BRIEF DESCRIPTION OF THE DRAWINGS

The summary, as well as the following detailed description, is further understood when read in conjunction with the appended drawings. For the purpose of illustrating the claimed methods, there are shown in the drawings exemplary embodiments of the methods; however, the methods are not limited to the specific methods disclosed. In addition, the drawings are not necessarily drawn to scale. In the drawings:

FIG. 7 illustrates a subset of neurons in the nodose ganglion that respond to pro-inflammatory cytokines. Calcium responses in vagal sensory neurons expressing the genetically encoded fluorescent calcium indicator GCaMP6s were imaged while administering cytokines intraperitoneally. The platform was modified to image the response of vagal sensory neurons to cytokines. The cytokine was administered via intraperitoneal injection and calcium activity in the nodose ganglion was monitored. Heat maps depicting z-score-normalized fluorescence traces from vagal neurons identified as responders of proinflammatory cytokine (TNFa). Neural activity was detected using an in-vivo calcium imaging platform with genetically encoded calcium indicator GCaMP6 expressed in all vagal sensory neurons. Each trial represents the activity of a single cell. Vertical dashed lines indicate the time of cytokine administration (intraperitoneal). Note the absence of response to vehicle control (Saline, 0.9% NaCl). Administration of pro-inflammatory cytokine triggered robust activity in a unique subset of vagal sensory neurons that are not activated by control stimuli like glucose or saline.

FIG. 12 illustrates the effect of neuronal stimulation in the caudal nucleus of the solitary tract on the immune response. Chemogenetic activation of the LPS-TRAPed population in the cNST strongly inhibited the LPS evoked release of pro-inflammatory cytokine TNFa and increased that anti-inflammatory cytokine IL-10. Neuronal populations were chemogenetically activated with designer receptor exclusively activated by a designer drug (DREADD) while the animal is given LPS and cytokine levels in the blood were measured. In the control animals, LPS induced the strong release of pro-inflammatory TNFa, reaching 200 pg/ml in the peripheral blood. When this brainstem neuronal population was activated with DREADD, there was a remarkable suppression of pro-inflammatory cytokine release, resulting in 90% reduction in the TNFa in the blood. The same results were obtained for another proinflammatory cytokine, IL-6. In addition to suppressing the release of pro-inflammatory cytokines, activation of this neuronal population markedly increase the release of the anti-inflammatory cytokine, IL-10. Thus, this brain circuit triggers a strong anti-inflammatory response while suppressing pro-inflammatory cytokines. Note that under normal conditions (control) the immune insult triggers a very large induction of pro-inflammatory cytokines (TNFa; left panels), and this induction is suppressed by activation of the cNST neurons (compare bars). In addition, activation of these same neurons triggers the strong induction of peripheral anti-inflammatory cytokines (IL-10; right panels) (compare bars).

FIG. 22 illustrates that vagal neurons mediate the body-brain immune modulation. Artificial activation of TRPA1-expressing neuron in the vagal ganglia (chemogenetically in this example) mimics the effect of activating the cNST neurons and leads to the suppression of pro-inflammatory cytokines, and the induction of anti-inflammatory cytokines.

FIG. 24 illustrates that an immune insult with LPS triggers strong innate immune responses, characterized by the release of proinflammatory cytokines like IL-1b, IL-6, and TNFa, and the release of anti-inflammatory cytokines that help modulate and dampen the inflammatory response, like IL-10. A balanced ratio of pro- and anti-inflammatory cytokines is important for an appropriate immune response

DETAILED DESCRIPTION OF ILLUSTRATIVE EMBODIMENTS

Figure 1:
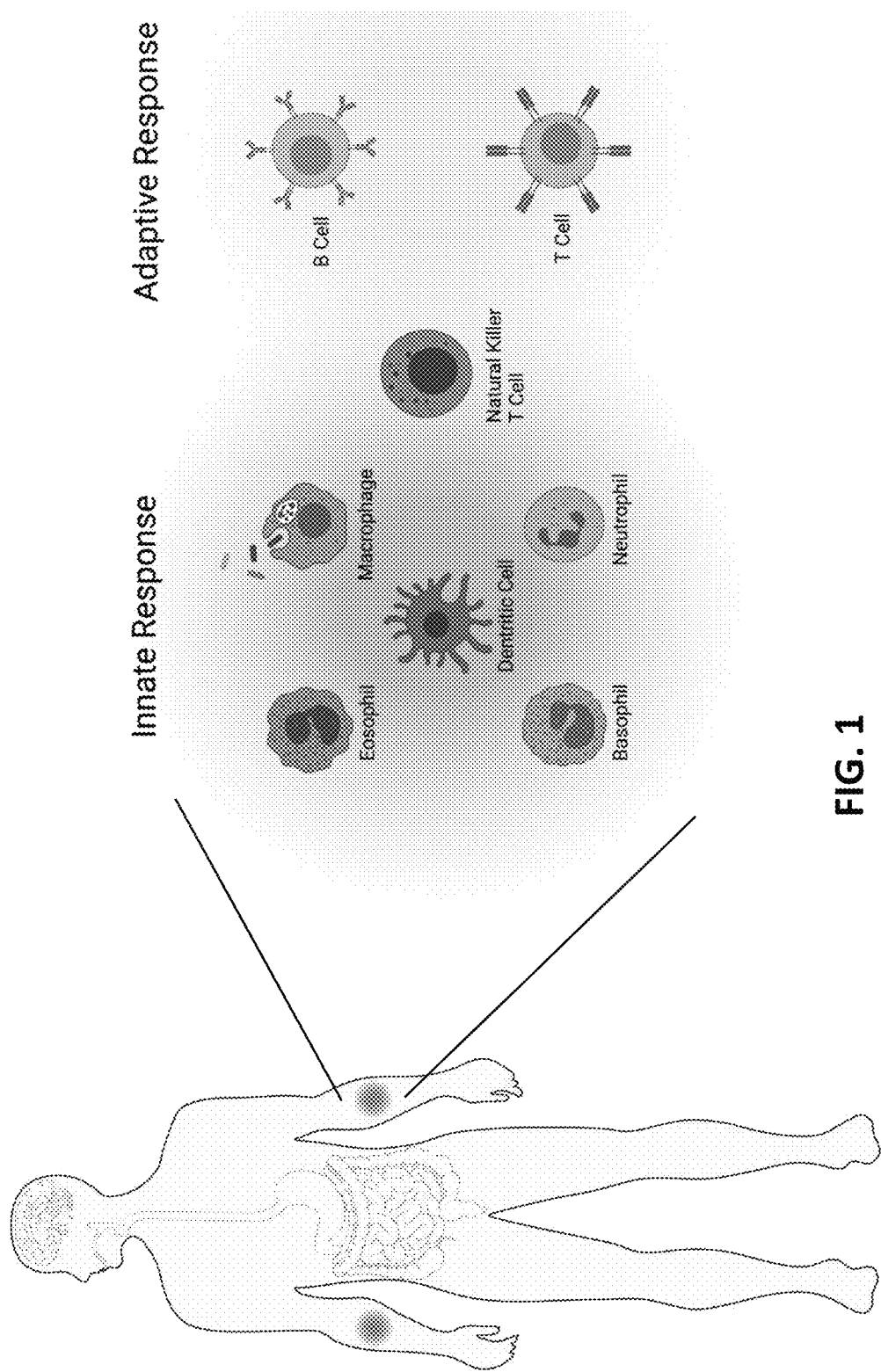
FIG. 1 illustrates the cellular components of the innate and adaptive immune response. Upon detection of an infectious agent, the immune system triggers and innate response followed by adaptive response. These two responses are executed by various cellular components as depicted and need to be tightly regulated to effectively combat an infection.
Figure 2:
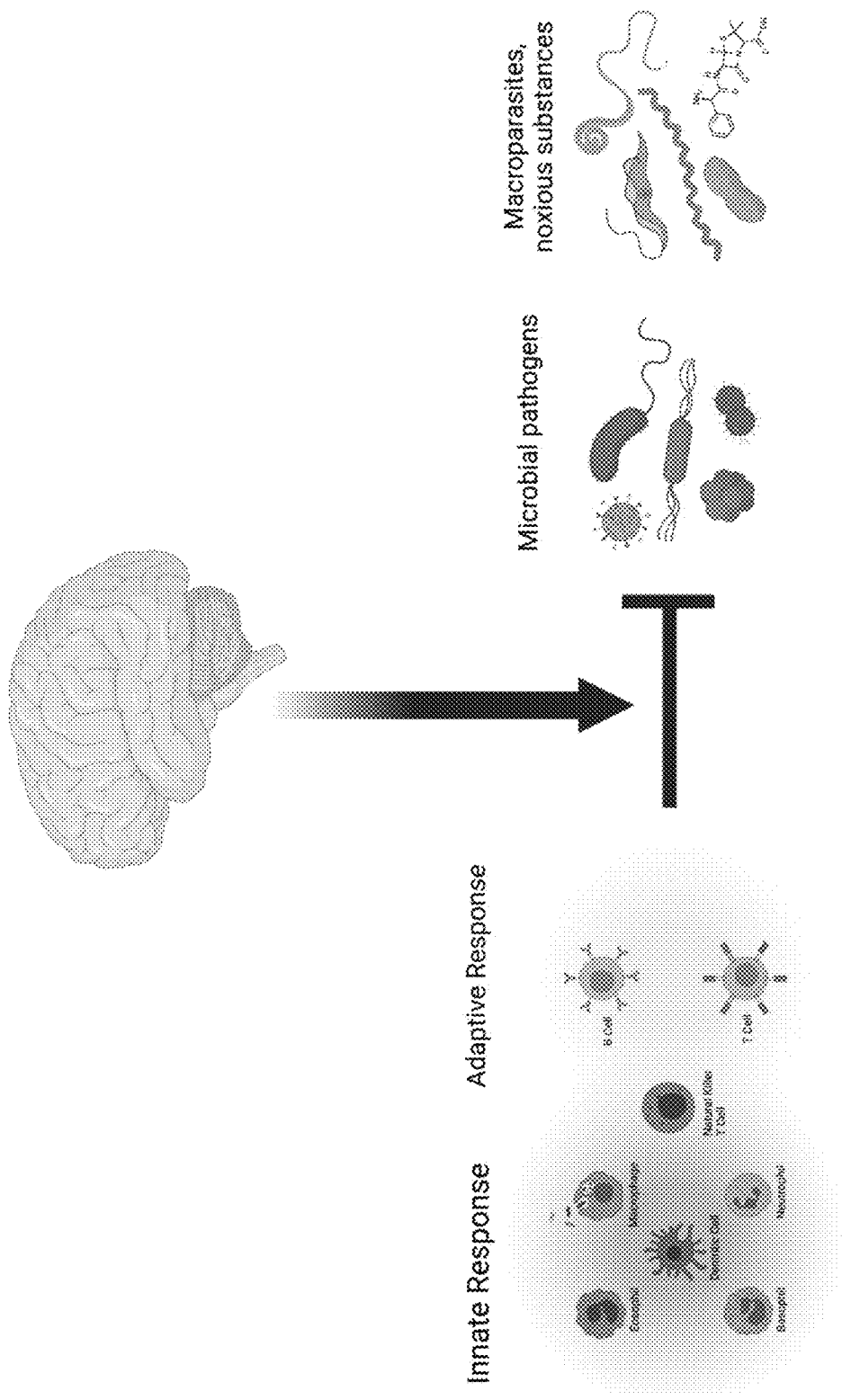
FIG. 2 depicts the central role of the brain in controlling immune responses. The brain plays an essential role in regulating the immune response although the exact regions that control and respond to immune activation were previously not well understood.
Figure 3:
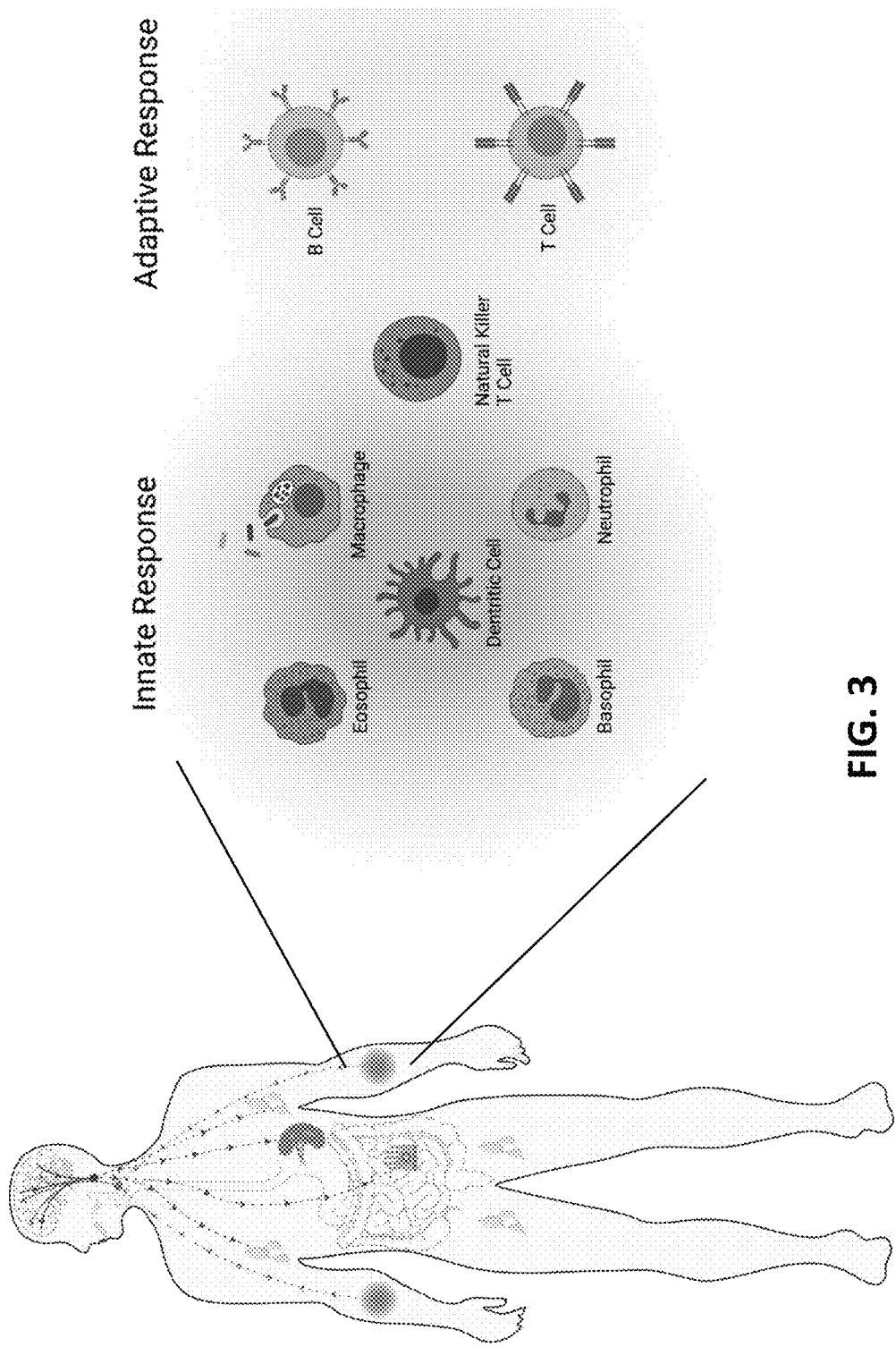
FIG. 3 illustrates the anatomical connection between the nervous system and the immune system. Anatomically there are extensive connections between the brain and the immune system. However, the functional significance of these connections in the neuronal control of immune response remains largely unknown.
Figure 4:
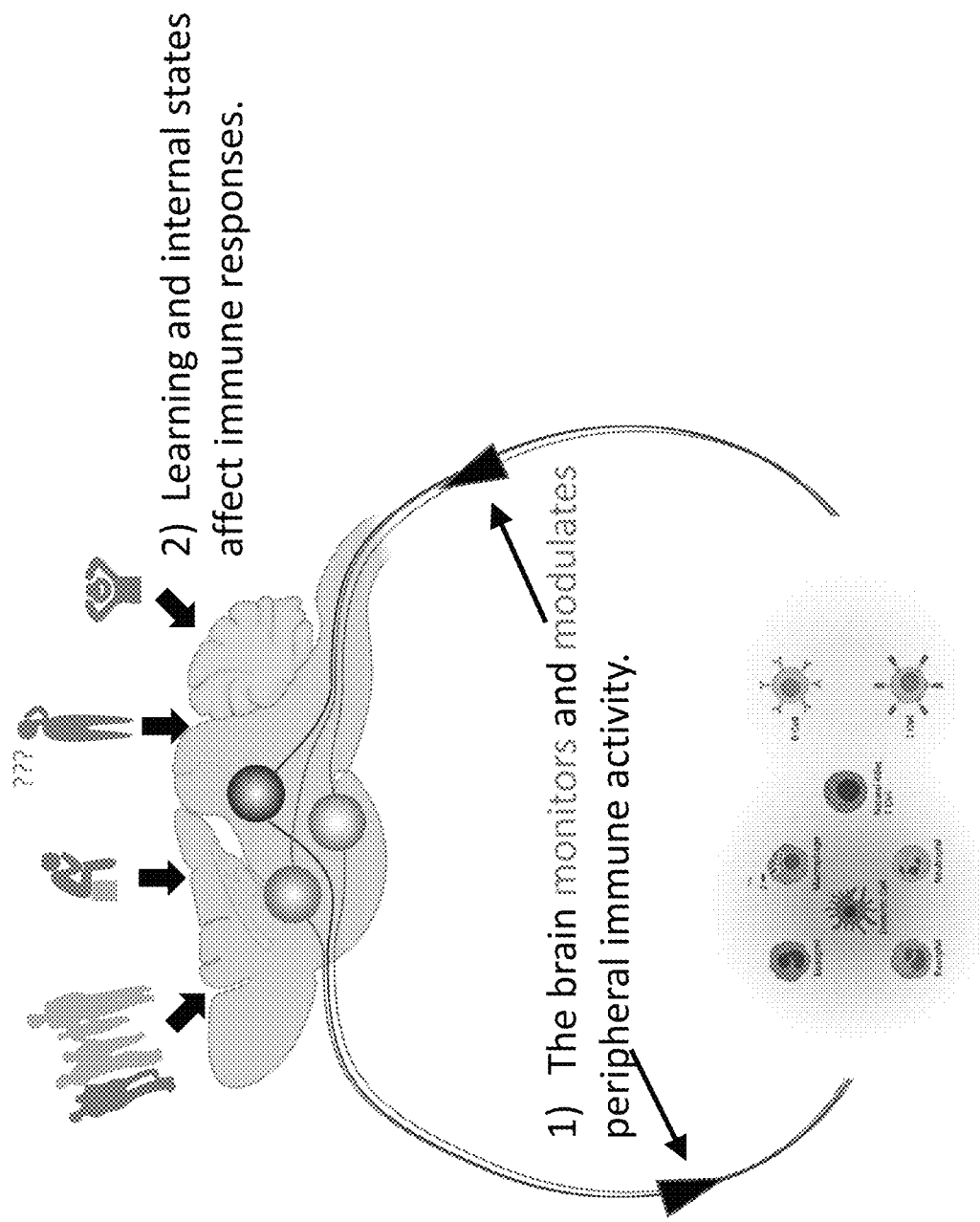
FIG. 4 depicts the effect of learning and internal states on the immune response. The brain detects peripheral immune activity and regulates peripheral immune response. Further, learning and internal states can regulate the immune response.

The disclosed methods may be understood more readily by reference to the following detailed description taken in connection with the accompanying figures and examples, which form a part of this disclosure. It is to be understood that this methods are not limited to the specific methods described and/or shown herein, and that the terminology used herein is for the purpose of describing particular embodiments by way of example only and is not intended to be limiting of the claimed methods. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the methods which are, for clarity, described herein in the context of separate embodiments, may also be provided in combination in a single embodiment. Conversely, various features of the methods that are, for brevity, described in the context of a single embodiment, may also be provided separately or in any subcombination. Further, reference to values stated in ranges include each and every value within that range.

Described herein are methods of regulating an immune response. In some embodiments, the methods of regulating an immune response in a mammal comprise modulating the activity of one or more TRPA1-expressing neurons in a vagal ganglion of the mammal to thereby regulate the immune response, wherein, when the neuron is engineered to express a designer receptor exclusively activated by a designer drug (DREADD), there is a decreased serum level of one or more proinflammatory cytokines and/or an increased serum level of one or more anti-inflammatory cytokines in the presence of a DREADD ligand.

In some embodiments, the methods of regulating an immune response in a mammal comprise modulating the activity of one or more CGRP receptor-expressing neurons in a vagal ganglion of the mammal to thereby regulate the immune response, wherein, when the neuron is engineered to express a DREADD, there is an increased serum level of one or more proinflammatory cytokines and/or a decreased serum level of one or more anti-inflammatory cytokines in the presence of a DREADD ligand.

In some embodiments, the methods of regulating an immune response in a mammal comprise modulating the activity of one or more neurons in the brainstem of the mammal, wherein, the neuron is activated by lipopolysaccharide (LPS) to induce release of pro-inflammatory cytokines, and wherein, when the neuron is engineered to express a DREADD, there is a reduced LPS-evoked release of pro-inflammatory cytokines and/or increased release of anti-inflammatory cytokines in the presence of a DREADD ligand.

Modulation of the neurons engineered to express a DREADD herein can result in an increased or decreased serum level of one or more proinflammatory cytokines and/or an increased or decreased serum level of one or more anti-inflammatory cytokines. The pro-inflammatory cytokines can comprise one or more of tumor necrosis factor, interleukin-6, and interluekin-1. The anti-inflammatory cytokines can comprise one or more of interleukin-10, interleukin-4, and tumor growth factor beta.

According to any one of the herein described methods, modulating the activity of one or more neurons can comprise activating the neuron. According to any one of the herein described methods, modulating the activity of one or more neurons can comprise inhibiting the neuron. Modulating the activity of one or more neurons according to any of the herein described methods can comprise administering an agent to the mammal. The agent modulating the activity of one or more neurons can be a small molecule. The agent modulating the activity of one or more neurons can be a biologic. In some embodiments, the agent activates the neuron. In some embodiments, the agent inhibits the neuron.

According to any one of the herein described methods, regulating the immune response comprises increasing or reducing a serum level of one or more pro-inflammatory cytokines and/or increasing or reducing a serum level of one or more anti-inflammatory cytokines. In some embodiments, the serum level of one or more pro-inflammatory cytokines is increased. In some embodiments, the serum level of one or more pro-inflammatory cytokines is decreased. In some embodiments, the serum level of one or more anti-inflammatory cytokines is increased. In some embodiments, the serum level of one or more anti-inflammatory cytokines is decreased. Changes in the levels of pro-inflammatory cytokines can accompany a change in the levels of anti-inflammatory cytokines. For example, decreased levels of one or more pro-inflammatory cytokines can accompany increased levels of anti-inflammatory cytokines or increased levels of one or more pro-inflammatory cytokines can accompany decreased levels of anti-inflammatory cytokines. The pro-inflammatory cytokines can comprise one or more of tumor necrosis factor, interleukin-6, and interleukin-1. The anti-inflammatory cytokines can comprise one or more of interleukin-10, interleukin-4, and tumor growth factor beta.

The DREADD used in any one of the herein described methods can be hM3Dq, hM1Dq, or hMD5q. In some embodiments, the DREADD is hM3Dq. In some embodiments, the DREADD is hM1Dq. In some embodiments, the DREADD is hMD5q. The DREADD ligand can be clozapine N-oxide (CNO).

According to the herein described methods, the mammal can have a cancerous disease, an autoimmune disease, an infectious disease, or an injury. In some embodiments, the mammal has a cancerous disease. In some embodiments, the mammal has an autoimmune disease. In some embodiments, the mammal has an infectious disease. In some embodiments, the mammal has an injury.

Also disclosed herein are methods to alter an immune response via chemogenetic activation of neurons in the mammal's caudal nucleus of the solitary tract. Regulation of the immune system encompasses means by which the immune response can be altered from its otherwise natural state. In some embodiments, alteration can include inducing, enhancing, or sustaining an immune response. In some embodiments, alternation can include preventing, suppressing, or shortening an immune response.

Also disclosed herein are methods to treat or suppress an inflammatory response in a mammal via chemogenetic activation of neurons in the mammal's caudal nucleus of the solitary tract. Treatment used herein describes the amelioration of a sign, symptom, or underling cause of a disease or condition. An inflammatory response can encompass any sign, symptom, or underlying cause related to immune system activation.

Chemogenetic activation in this method can be accomplished through a DREADD. Examples of DREADDs include, but are not limited to hM3Dq, hM1Dq, or hMD5q. Transformation of nucleic acids encoding a DREADD into neurons of interest can be accomplished though any means sufficient for transfection of nucleic acid into cells. Chemogenetic activation via a DREADD employs a ligand to which the DREADD can respond by activation. Exemplary ligands include, but are not limited to, clozapine N-oxide.

Activation of neurons via chemogenetic activation or immunostimulation can be verified or measured by any established method for determining or imaging neuronal activity including but not limited to assessment of c-fos induction or targeted recombination in active populations (TRAP).

The disclosed methods can result in or be used to reduce the levels of pro-inflammatory cytokines that exist in the serum or blood of a mammal. Pro-inflammatory cytokines are those capable of inducing, enhancing, or sustaining an immune response. Examples of pro-inflammatory cytokines include, but are not limited to, tumor necrosis factor, interleukin-6, and interluekin-1.

The disclosed methods can result in or be used to increase the levels of anti-inflammatory cytokines that exist in the serum or blood of a mammal. Anti-inflammatory cytokines are those capable of preventing, suppressing, or shortening an immune response. Examples of anti-inflammatory cytokines include, but are not limited interleukin-10, interleukin-4, and tumor growth factor beta.

The disclosed methods can be used on a mammal that has a disease, injury, or other state where immune regulation serves a purpose. Due to the role of the immune system in disease and injury states, altering an immune response in a manner beneficial to amelioration of a disease or injury state is contemplated by the disclosure. Regulation of the immune response can be for purposes that include but are not limited to inducing or preventing an immune response, activating or suppressing and immune response, or sustaining or shortening an immune response. Disease states that could benefit from regulation of an immune response include, but are not limited to cancerous diseases, autoimmune diseases, or infectious diseases. Any disease, or symptom thereof, which can be improved by immune system regulation or treatment and suppression of an inflammatory response could benefit from the described methods.

Animals suitable for the methods described include mammals, especially those with brain regions that contain a caudal nucleus of the solitary tract and vagus nerve or homologous structures whose activation can regulate the immune response.

Also disclosed herein are methods of screening therapeutic compounds to assess their ability to alter the immune response. The screening method can comprise a mammal expressing a genetically encoded calcium indicator (GECI) in the nodose ganglion region of the mammal's brain. The GECI can be any known in the art and suitable to assess the activation of the relevant neurons in the nodose ganglion including but limited to GCaMP. Signal from the GECI can comprise florescence, luminescence, or any other means to determine neuron activation. Any therapeutic agent can be assessed for its ability to alter an immune response via administration through a variety of routes, including but not limited to, intraperitoneal, subcutaneous, or intravascular. Therapeutic agents can encompass any substance with potential benefits to the mammal after administration which can include but are not limited to small molecule compounds, antibodies, a proteins, nucleic acids, or any combination thereof. The screening method comprises detecting signal in neuronal subsets activated by pro-inflammatory cytokines and neuronal subsets activated by anti-inflammatory cytokines as described herein following administration of a therapeutic agent.

EXAMPLES

A brainstem circuit that functions as a conduit to convey peripheral immune information to the brain was identified. Activation of this circuit can trigger robust suppression of peripheral immune activity. Using an activity marker (cFos induction), it was determined that a selective population of neurons in the brain are activated in response to administration of a peripheral immune insult.

An immune insult with LPS triggers strong innate immune responses, characterized by the release of proinflammatory cytokines like IL-1b, IL-6 and TNFa, and the release of anti-inflammatory cytokines, like IL-10, that help modulate and dampen the inflammatory response. A balanced ratio of pro- and anti-inflammatory cytokines is important for an appropriate immune response.

Figure 5:
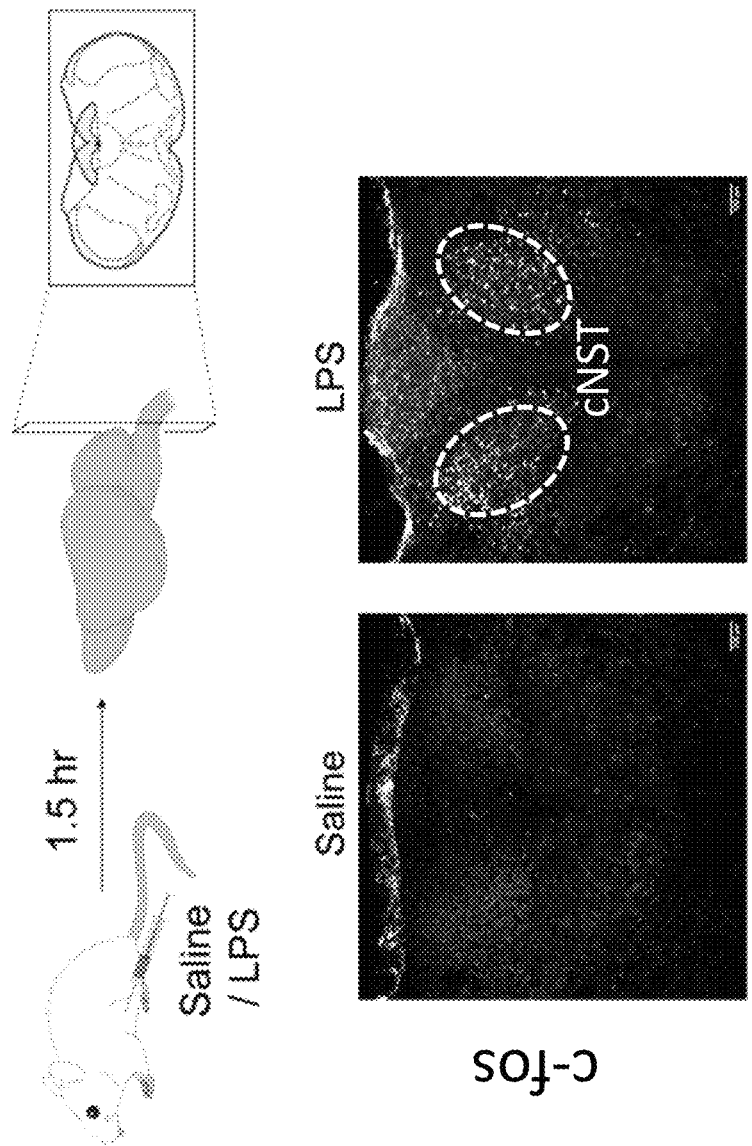
FIG. 5 shows a schematic of LPS stimulation strategy for Fos Induction and illustrates neuron activation in the caudal nucleus of the solitary tract upon immune system stimulation. Peripheral immune challenge evokes brain activities. LPS was used to induce an innate immune response and the brain was examined for the induction of c-fos as a proxy for neural activity. Strong Fos induction is observed in the caudal nucleus of the solitary tract (cNST, highlighted) in response to LPS stimulus but not control stimulus. When the body experiences bacterial infections, the bacterial membrane component lipopolysaccharide (LPS) triggers strong innate immune response. LPS (right) but not saline control (left) strongly activates cNST (circled area). For each condition, a representative image from N>=3 animals is shown. Scale bar: 100 μm. Strong bilateral c-fos labeling was detected in the caudal nucleus of the solitary tract (cNST) in the brainstem.
Figure 6:
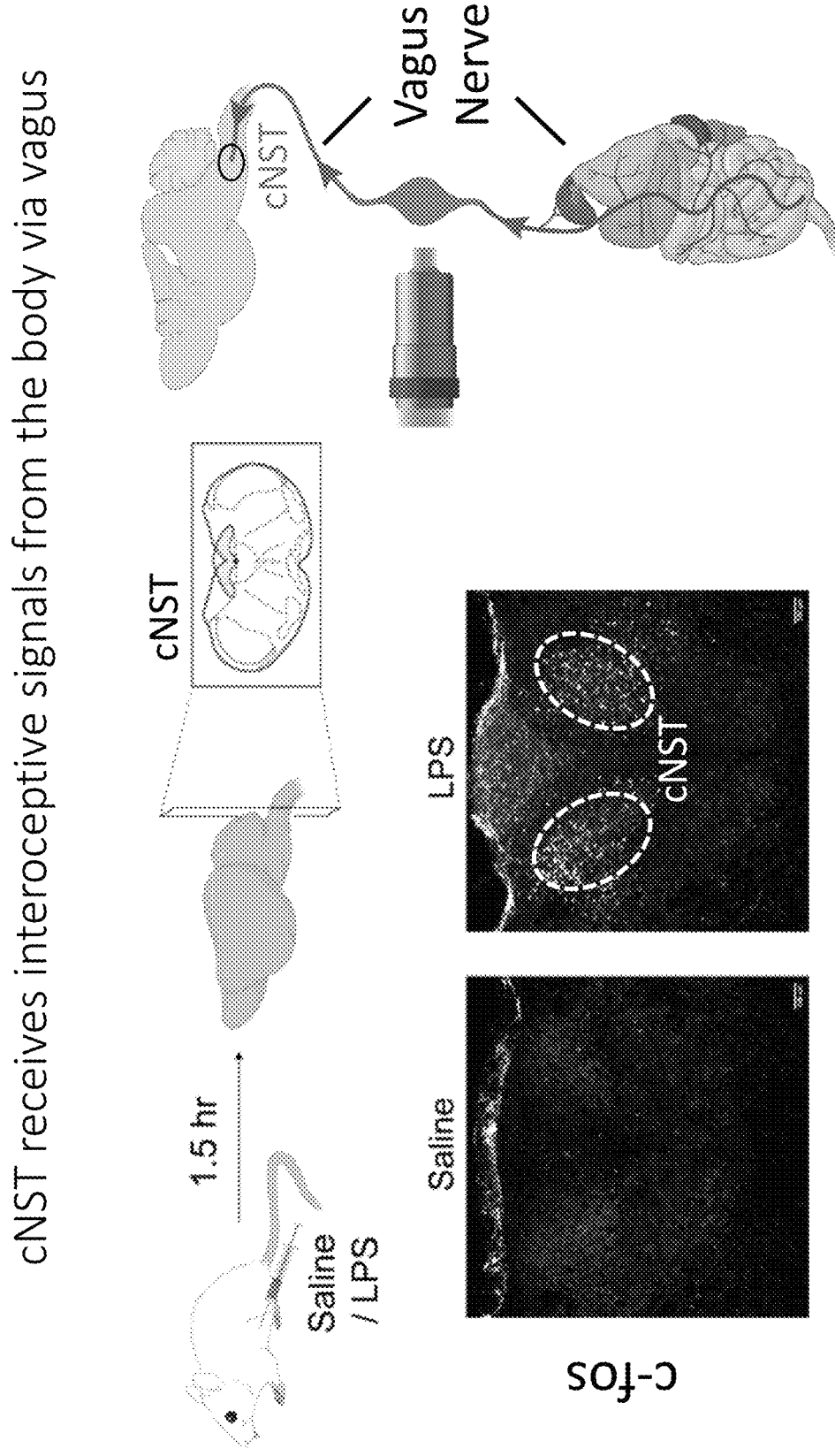
FIG. 6 depicts the role of the vagus nerve in transmitting signals between the caudal nucleus of the solitary tract and the peripheral immune response. cNST is a central hub of interception receiving body-wide physiological signals via the vagus nerve. Monitoring the vagal response to immune signals at this gateway to brain provides an understanding of how the brain monitors peripheral immune activities.
Figure 11:
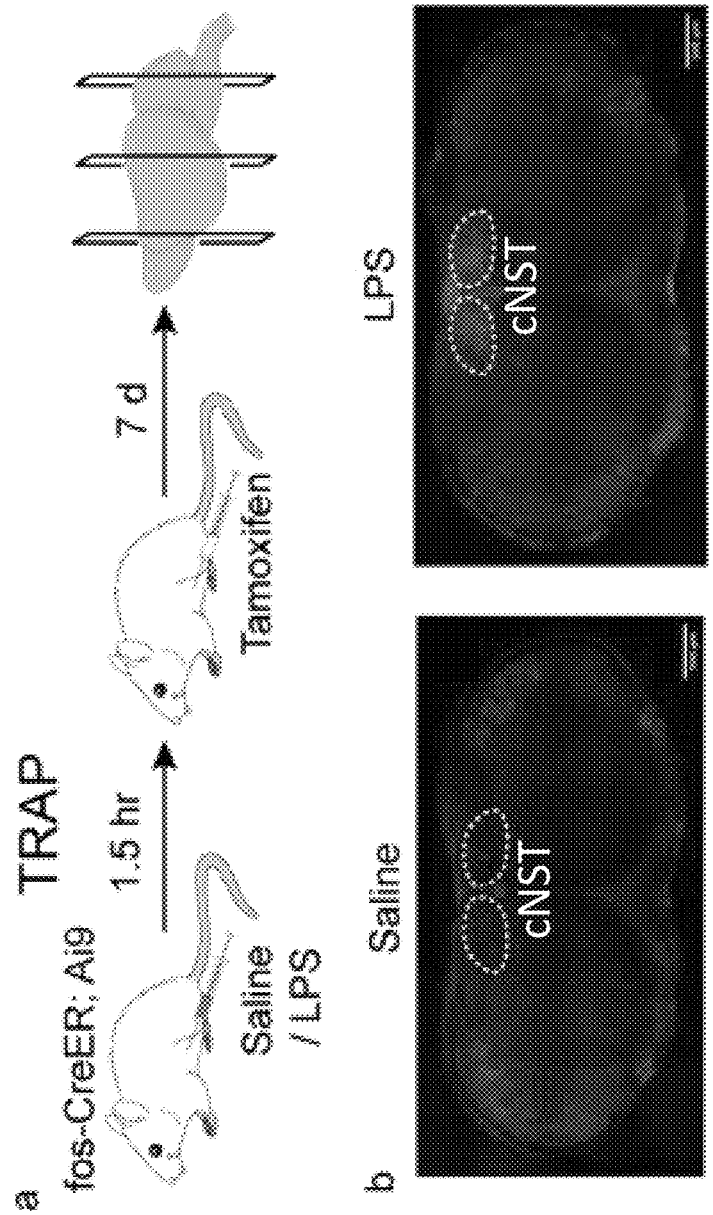
FIG. 11 shows a schematic of TRAP strategy to mark LPS-responsive neurons in the cNST (highlighted) with a fluorescent reporter (tdTomato) and illustrates neuron activation in the caudal nucleus of the solitary tract upon immune system stimulation using an activity based labeling strategy. The activity based labelling strategy, TRAP, was used to identify and access neuronal populations activated during LPS induced inflammation. Neurons TRAPed by LPS (right) but not saline control (left) are seen in the cNST (circled area). For each condition, a representative image from N>=3 animals is shown. Scale bar: 500 μm. Strong labelling with a florescence reporter is observed in the caudal nucleus of the solitary tract, the central target of vagal afferents, in LPS-treated animals but not saline treated animals.

It was shown that neurons in the caudal nucleus of the solitary tract (cNST) in the brainstem are activated by peripheral (intraperitoneal) administration of LPS (lipopolysaccharide), a potent inducer of inflammatory responses (FIG. 5). An activity-based labeling strategy (targeted recombination in active populations, TRAP) was employed to genetically access the LPS-activated neurons in the cNST (FIG. 11), and demonstrated that chemogenetic activation of these LPS-TRAPed cNST neurons robustly suppresses LPS-evoked the release of pro-inflammatory cytokines (e.g., TNFa) while enhancing the release of anti-inflammatory cytokines (e.g., IL10) (FIG. 12). In other words, the brain monitors and modulates immune responses in the body. These results open up unique opportunities to significantly modulate immune/inflammatory responses by acting on the nervous system. Next, to uncover the role of these cNST neurons in immune responses, a chemogenetic silencer was introduced by genetic Trapping, and the effect of silencing these cNST neurons in the emergence of LPS-induced inflammatory responses was evaluated.

Figure 18:
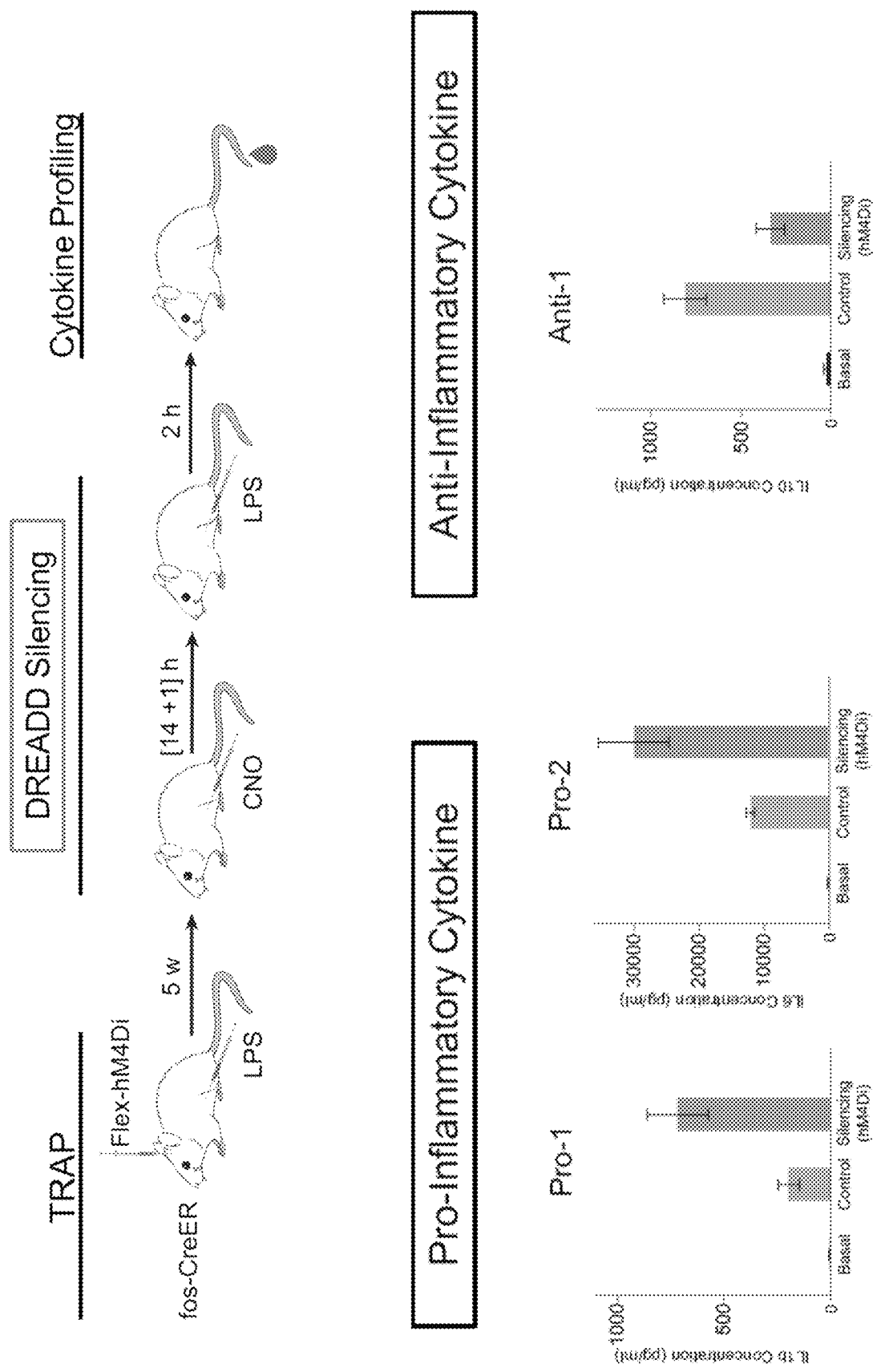
FIG. 18 shows that silencing cNST-responsive neurons de-suppresses inflammatory responses. Through utilization of genetic trapping and introduction of a chemogenetic silencer, the effect of silencing on cNST neurons in the emergence of LPS-induced inflammatory responses was investigated. When LPS-activated cNST neurons are silenced, there is a complete change in the inflammatory response: an out-of-control increase in the release of proinflammatory cytokines and a dramatic dampening in the release of anti-inflammatory cytokines.

In a normal response, LPS triggers the release of proinflammatory and anti-inflammatory cytokines, resulting in a balanced and controlled immune reaction. However, when this LPS-activated cNST neurons are silenced, there is a complete change in the inflammatory response: an out-of-control increase in the release of proinflammatory cytokines and a dramatic dampening in the release of anti-inflammatory cytokines (FIG. 18).

Figure 13:
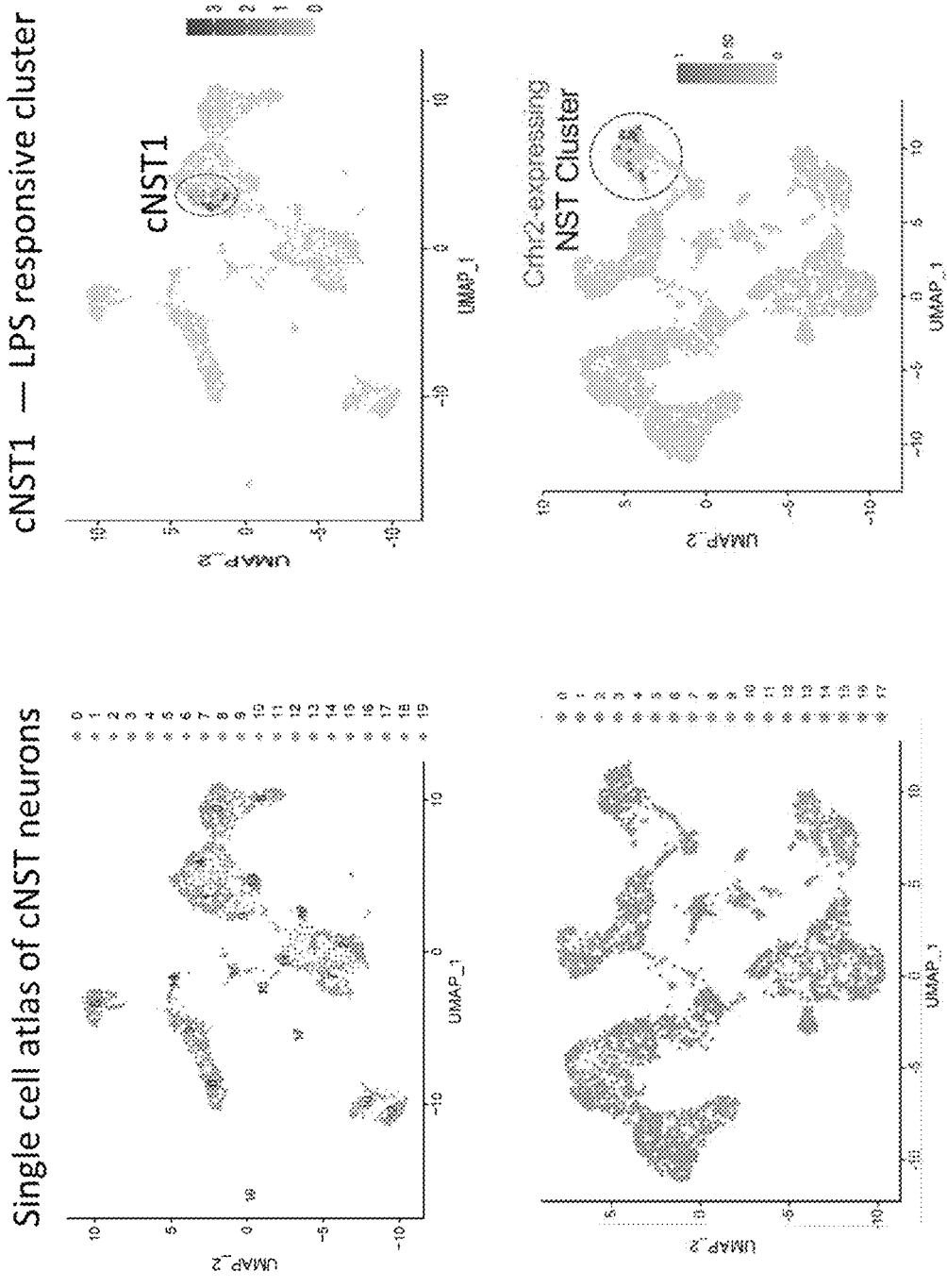
FIG. 13 illustrates a single cell atlas that maps neurons responsive to immune activation into a specific cluster. Using a single cell atlas of cNST, LPS responsive neurons map to a small cluster, cNST1.
Figure 14:
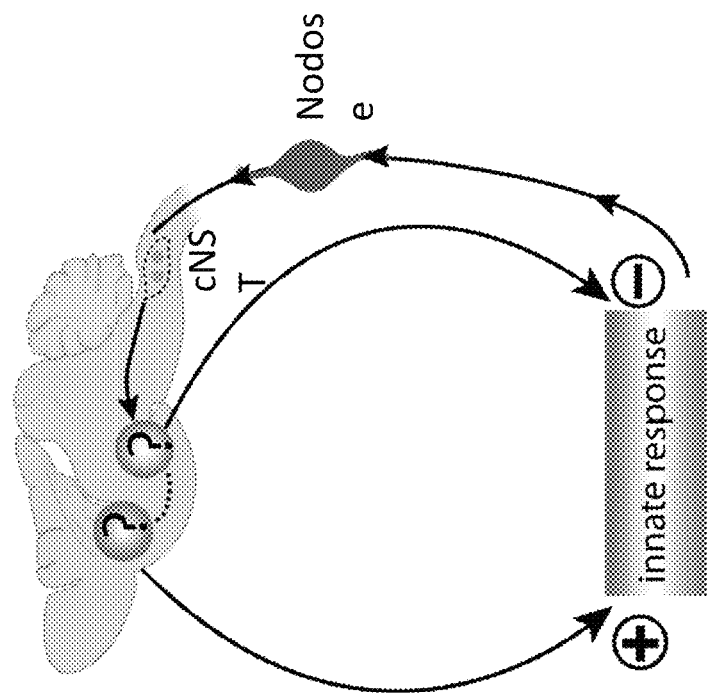
FIG. 14 depicts the bidirectional relationship between activation of neurons in the caudal nucleus of the solitary tract and regulation of the peripheral immune response. Identification of immune enhancing circuits within the brain. Immune responsive vagal and cNST neurons regulate peripheral immune information.
Figure 15:
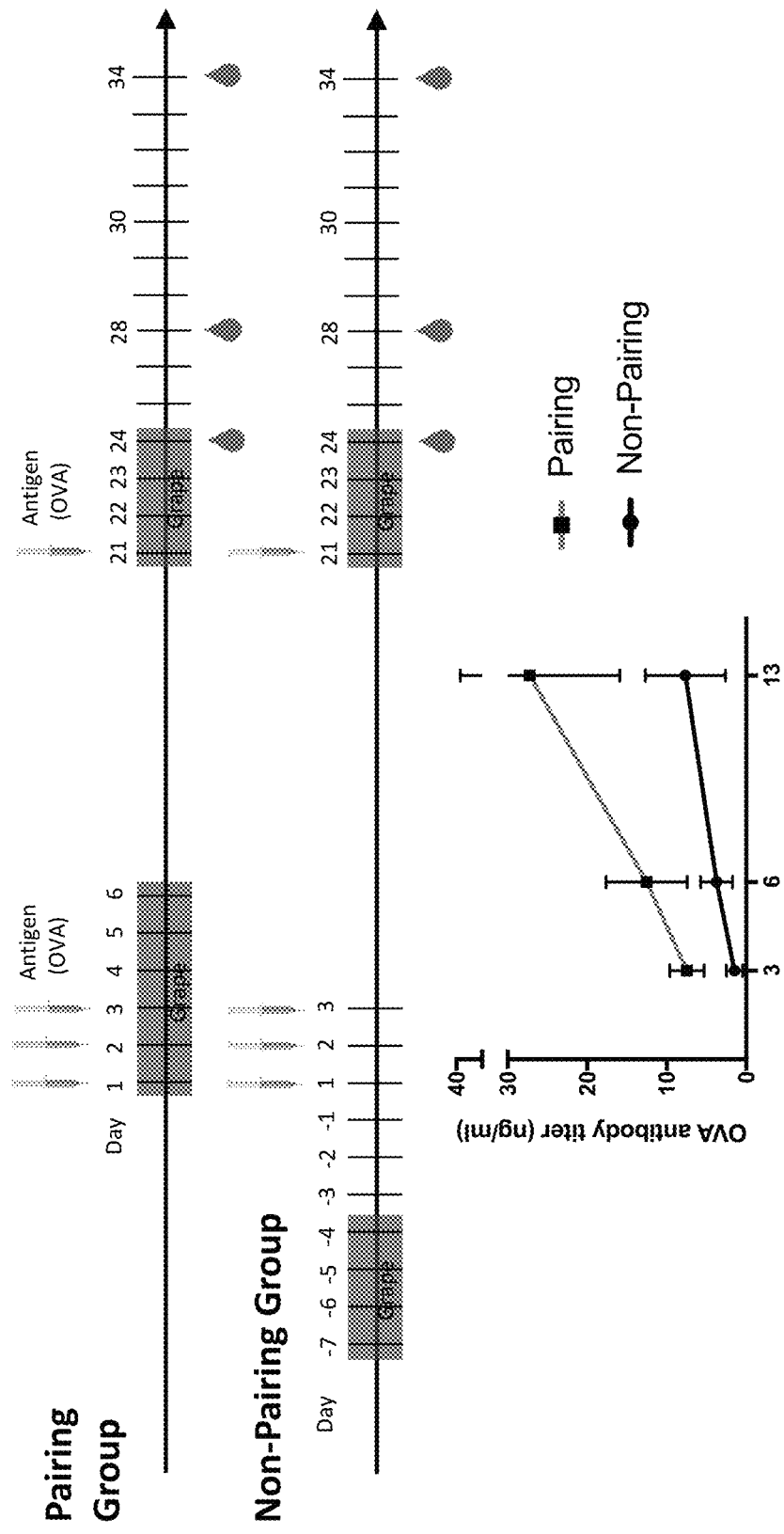
FIG. 15 illustrates the effect of learning on an adaptive immune response. Learning can profoundly influence peripheral immune function such that an anticipatory cue through learning can potentiate the immune response. In an immune-conditioning paradigm, mice were given an antigenic stimulus, ovalbumin, in the presence of grape water for three consecutive days while in the control group, grape water was given four days before ovalbumin administration. Significantly higher antibody titer was observed following re-exposure to ovalbumin and grape odor in the test group compared to the control, suggesting that grape odor is effectively conditioned mice to enhance immune response.
Figure 16:
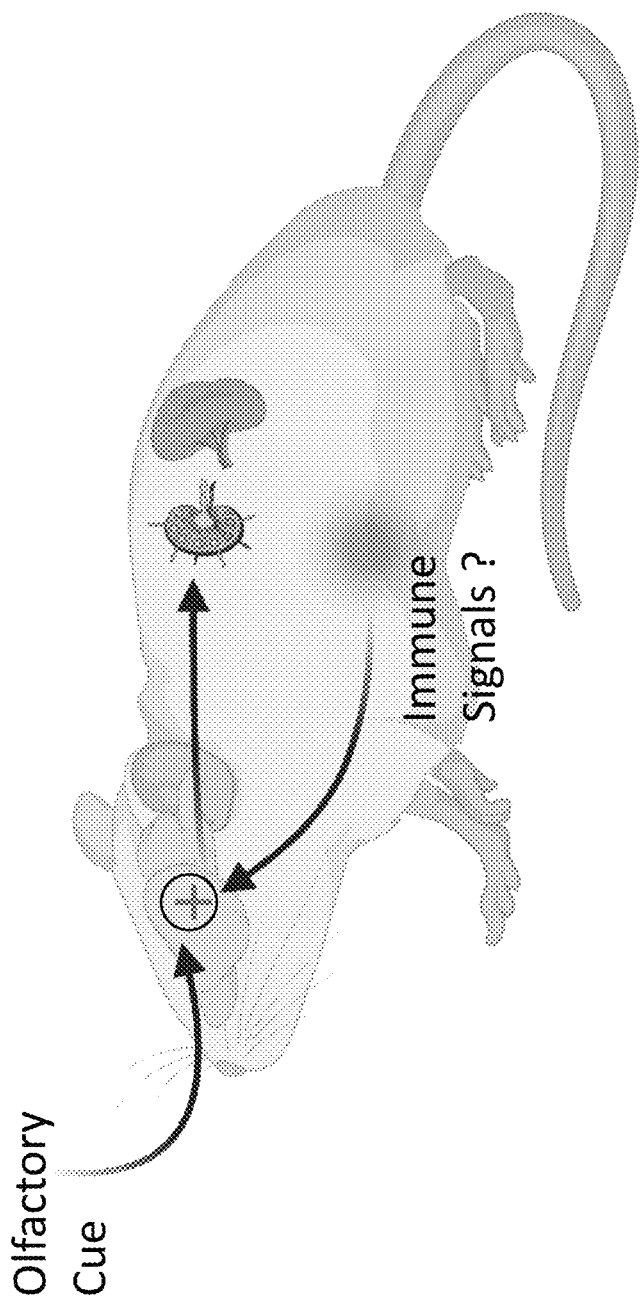
FIG. 16 depicts the relationship between olfactory cues and adaptive immune system regulation. The brain associates the immune signal with the sensory cue (grape odor, the conditioned stimulus) to impart the otherwise neutral olfactory cue with an immune modulating capacity.
Figure 17:
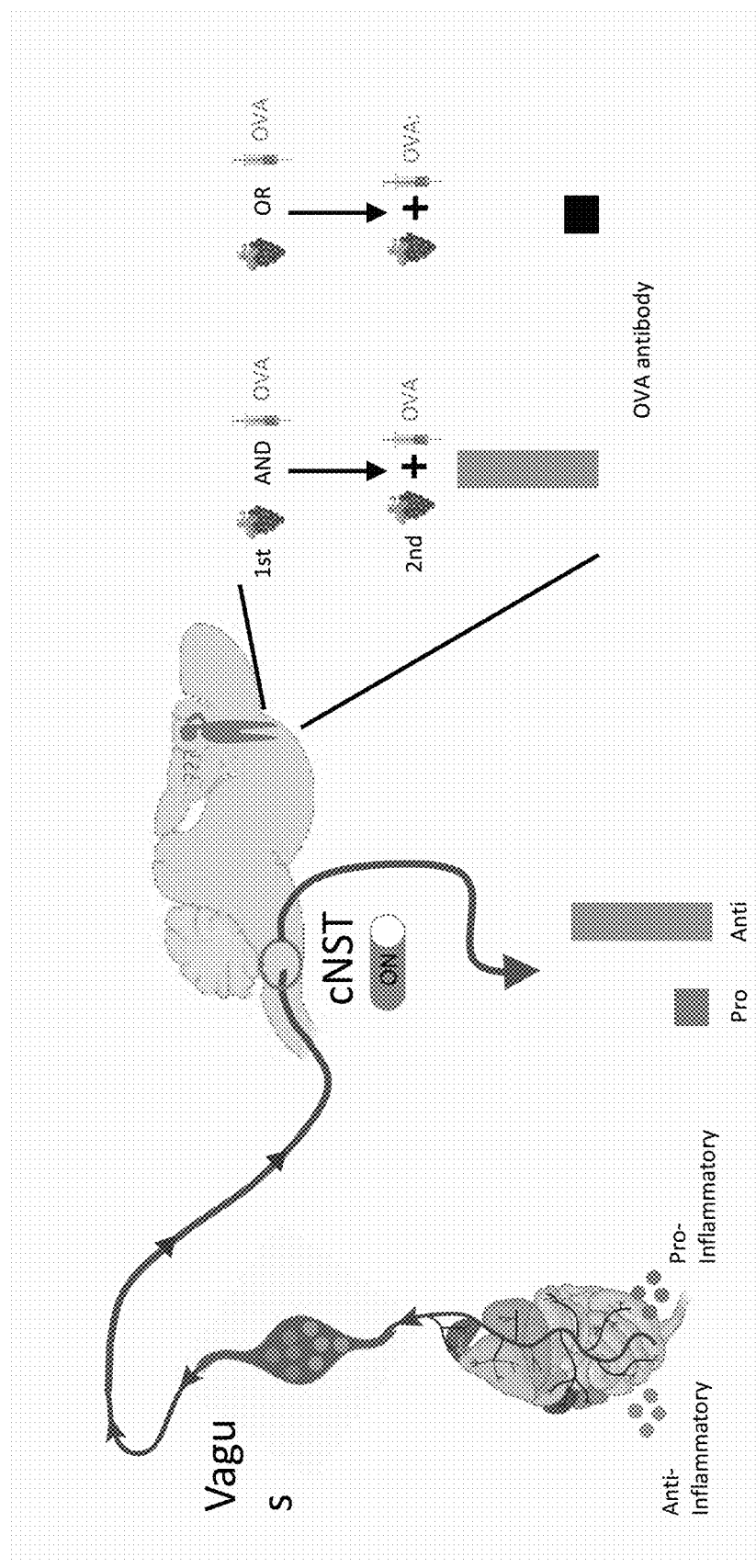
FIG. 17 depicts the relationship between neuronal activation, learned activity, and immune system regulation. The vagal-brainstem circuit reports and regulates peripheral immune responses. Vagal sensory neurons contain distinct subsets that respond to pro- and anti-inflammatory cytokines. Activating brainstem neurons receiving vagal input dramatically alters the nature of innate immune response. An immune-conditioning paradigm shows that predictive cues can impact immune responses.

A single cell atlas of the cNST was generated and ACT-Seq was used to identify the LPS-activated neurons: Corticotropin releasing hormone receptor-2 expressing neurons. A Cre driver line was then generated to manipulate their function, a chemogenetic activator was introduced, and it was shown that activating this unique, genetically identified cNST population, is sufficient to modulate the course of the inflammatory responses (FIG. 13).

Figure 19:
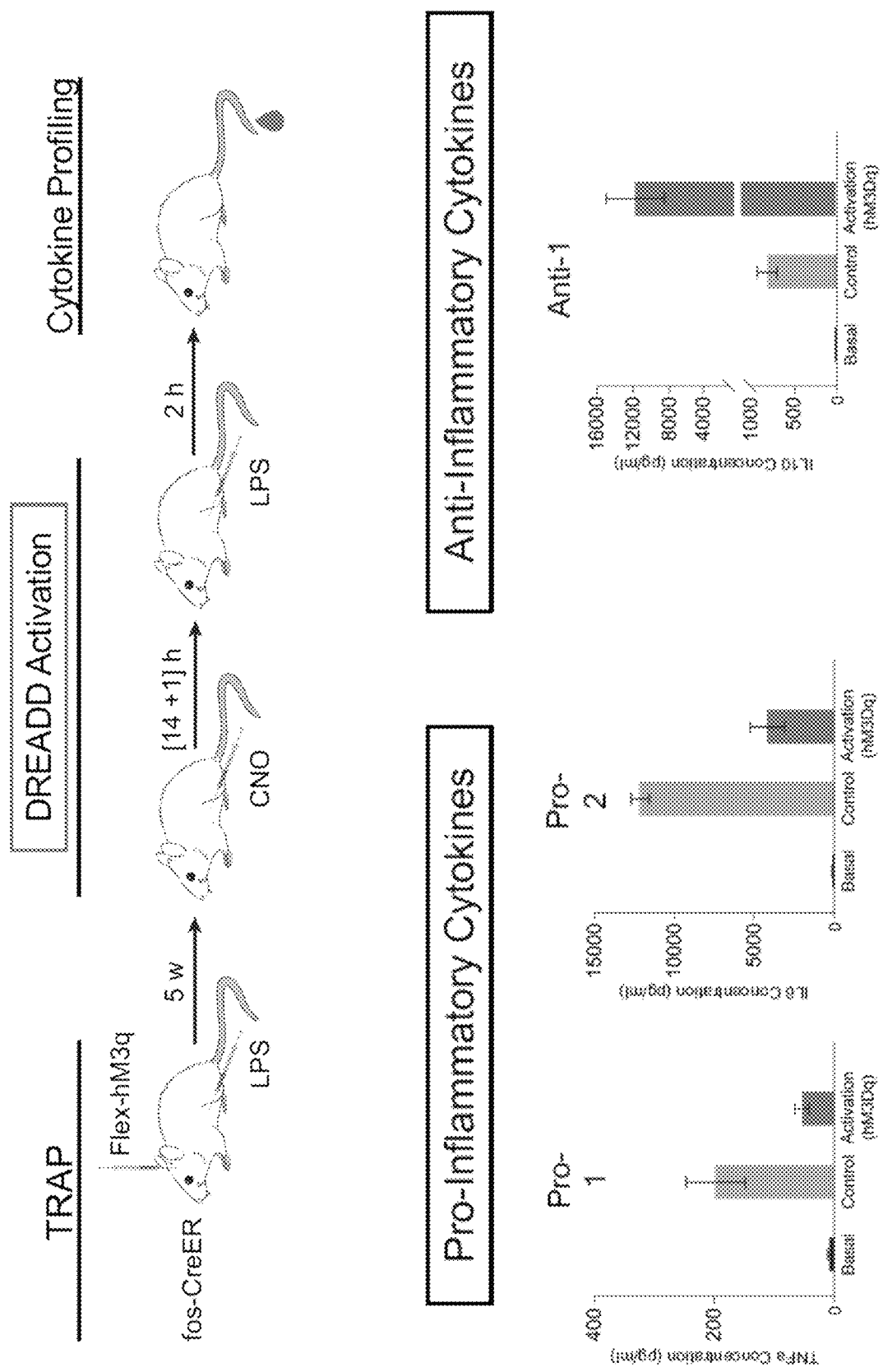
FIG. 19 illustrates that activating cNST-responsive neurons dramatically suppresses inflammatory responses. Though utilization of the TRAP system and selective chemogenetic activation, the effect after LPS injection on the neurons was examined. These neurons were artificially activated after LPS using a synthetic drug, CNO, and then cytokine levels in the circulation were analyzed in response to LPS. Activating these neurons leads to a dramatic suppression of the release of pro-inflammatory cytokines, accompanied with a very large increase in the levels of anti-inflammatory cytokines.
Figure 20:
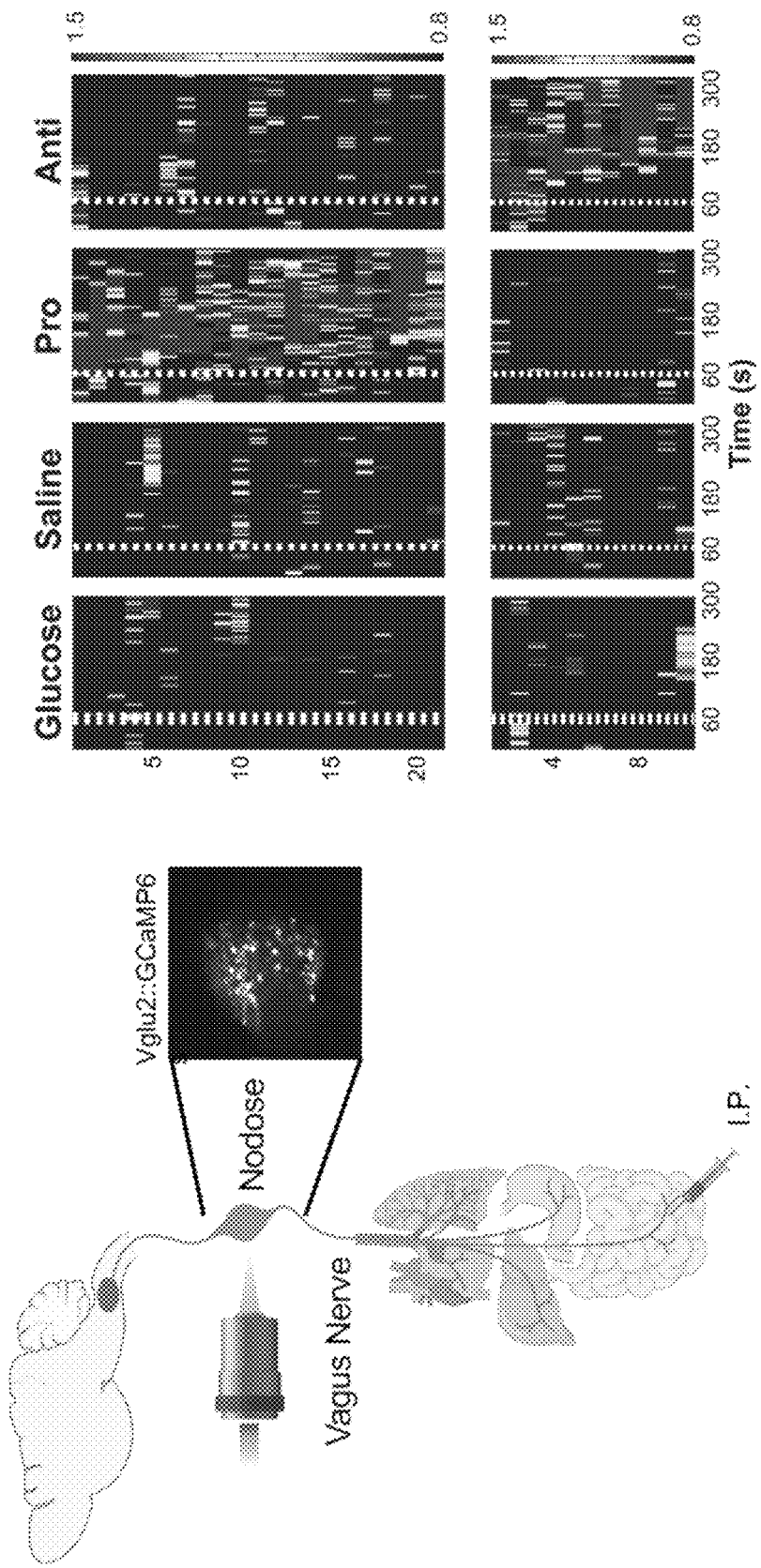
FIG. 20 shows imaging of vagal sensory neuron responses to pro- & anti-inflammatory cytokines. There is a selective population of neurons that responds to pro-inflammatory cytokines, and a separate population that responds to anti-inflammatory cytokines.

The TRAP system was used to gain genetic access to these neurons, and selectively activating them chemogenetically. The effect of activation after LPS injection could then be examined. Activating these neurons leads to a dramatic suppression of the release of pro-inflammatory cytokines, accompanied with a very large increase in the levels of anti-inflammatory cytokines, in essence a transformation of the inflammatory response (FIG. 19). These results provide a powerful strategy to suppress inflammatory responses and the inflammatory state. This strategy could be deployed to help manage autoimmune disorders, cytokine storm responses, graft-vs-host reactions, cancer immunotherapies, toxic shock syndrome, etc.

Figure 8:
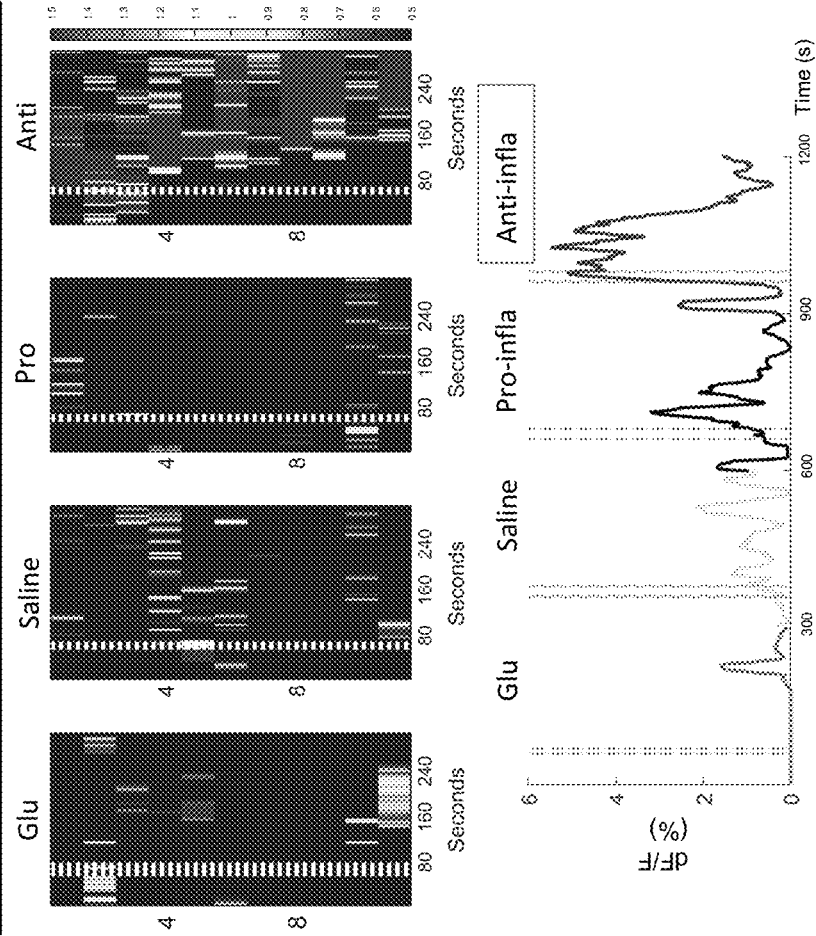
FIG. 8 illustrates a subset of neurons in the nodose ganglion that respond to anti-inflammatory cytokines. Heat maps depicting z-score-normalized fluorescence traces from vagal neurons identified as responders of anti-inflammatory cytokines (IL-4). Each row represents the activity of a single cell. Vertical dashed lines indicate the time of cytokine administration (intraperitoneal). Note the absence of response to vehicle control (Saline, 0.9% NaCl). Neural activity was detected using an in-vivo calcium imaging platform with genetically encoded calcium indicator GCaMP6 expressed in all vagal sensory neurons. The platform was modified to image the response of vagal sensory neurons to cytokines. The cytokine was administered via intraperitoneal injection and calcium activity in the nodose ganglion was monitored. Administration of anti-inflammatory cytokine triggered robust activity in a unique subset of vagal sensory neurons that are not activated by control stimuli like glucose or saline.
Figure 9:
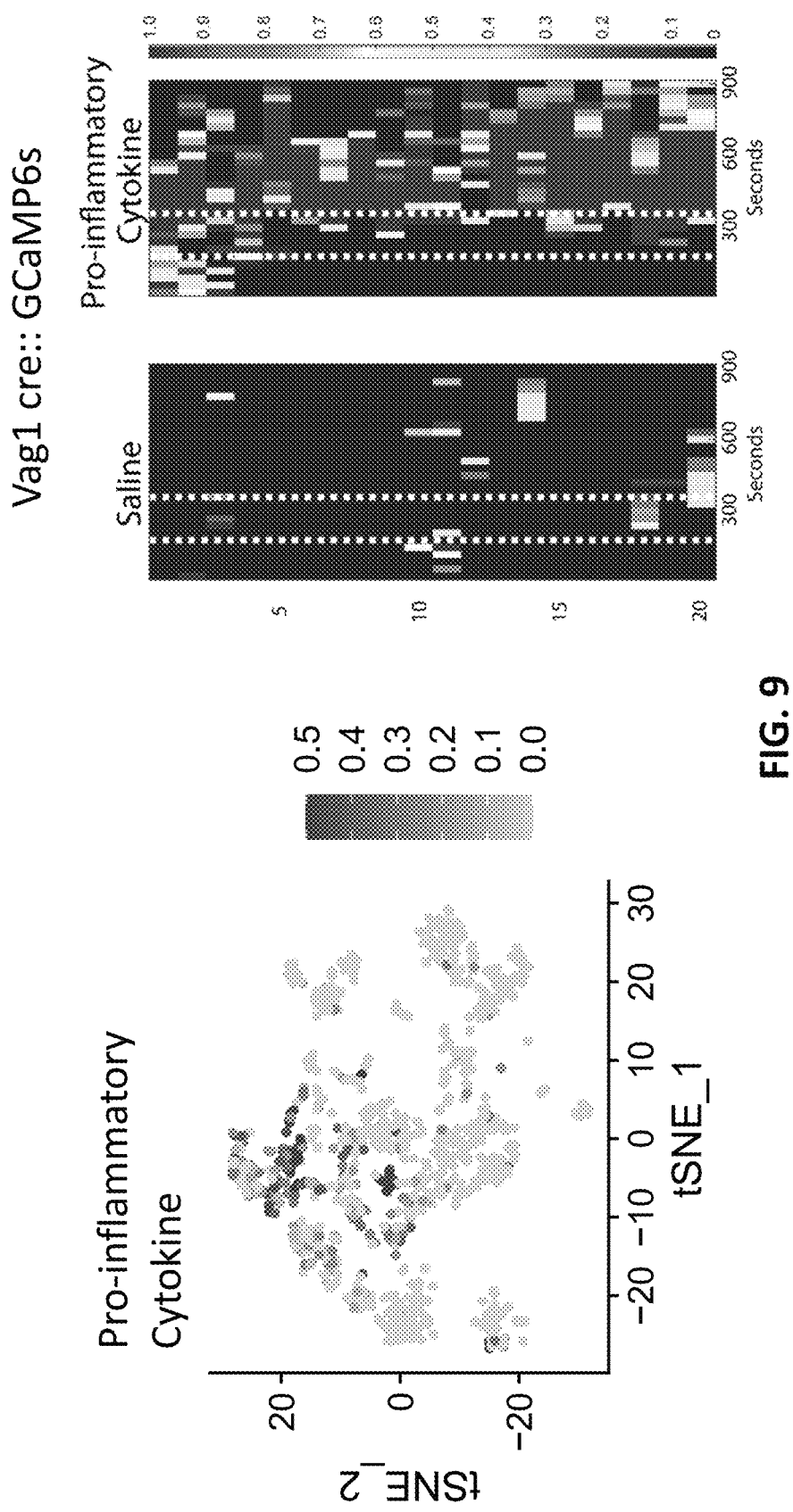
FIG. 9 illustrates the mapping of the receptor for pro-inflammatory cytokines. Heat maps depicting z-score-normalized calcium responses of VIP expressing vagal neurons to pro-inflammatory cytokine stimulation (bath application for 3 mins). Each trial represents the activity of a single cell. Dashed lines indicate stimulation time window. Approximately 30% of VIP neurons respond. The receptor for pro-inflammatory cytokine was mapped to a small cluster by exploiting the single cell atlas of vagal sensory neurons. Using the cre driver to express GCaMP in this cluster, this cluster enriches neurons that are activated by pro-inflammatory cytokine.
Figure 10:
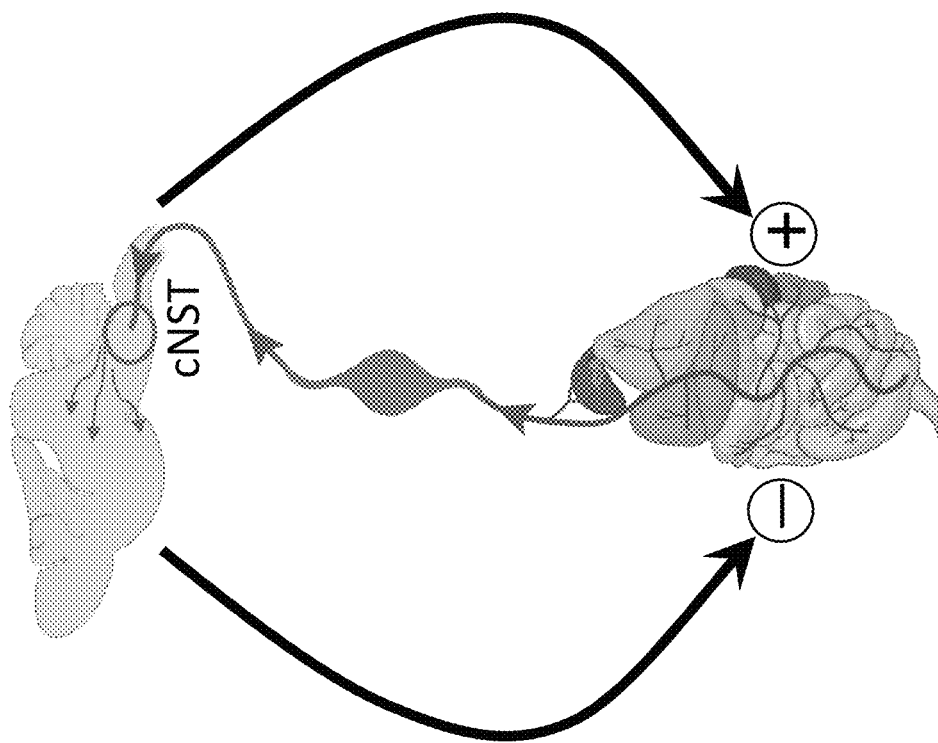
FIG. 10 depicts the relationship between the caudal nucleus of the solitary tract in regulating the peripheral immune response. The brain uses information conveyed by vagal sensory neurons to positively and negatively feedback modulate immune response.

One of the main pathways of information between the body and the brain is the vagal nerve, thus vagal sensory neurons activation in response to immune signals was analyzed. Using an imaging platform to record activity from vagal ganglia, it was shown that a selective subset of vagal sensory neurons respond robustly and reliably to administration of proinflammatory cytokines (e.g., TNFa & IL1b) (FIG. 7), and further demonstrated that this population of neurons is defined by the expression of the vasoactive intestinal peptide (VIP) gene (FIG. 9). Importantly, a separate population of vagal neurons that are activated by stimulation with anti-inflammatory cytokines (e.g., IL4; FIG. 8) was also identified.

Given that vagal sensory neurons transmit information to the brain by synapsing with targets in the caudal nucleus of the solitary tract (cNST) in the brainstem (see FIG. 5), the results provide a direct path to modulate this brain circuit either peripherally (i.e., via vagal neurons) or centrally (i.e., via cNST neurons).

Figure 21:
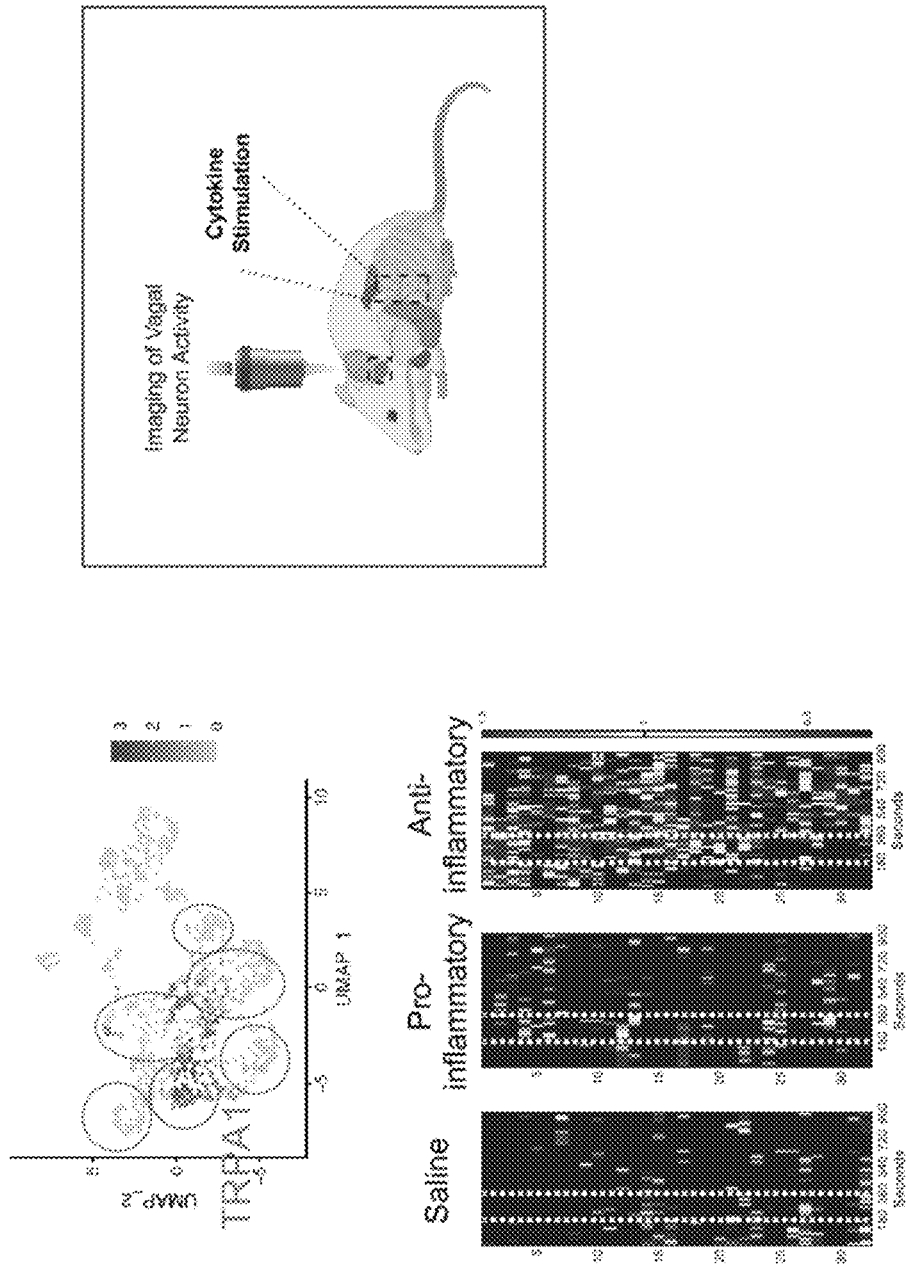
FIG. 21 shows genetic identification of vagal neurons responding to pro-inflammatory signals. A single cell atlas of the vagal ganglia (Nodose), combined with functional imaging demonstrate that TrpA1-expressing neurons in the vagal ganglia respond to anti-inflammatory signals.
Figure 23:
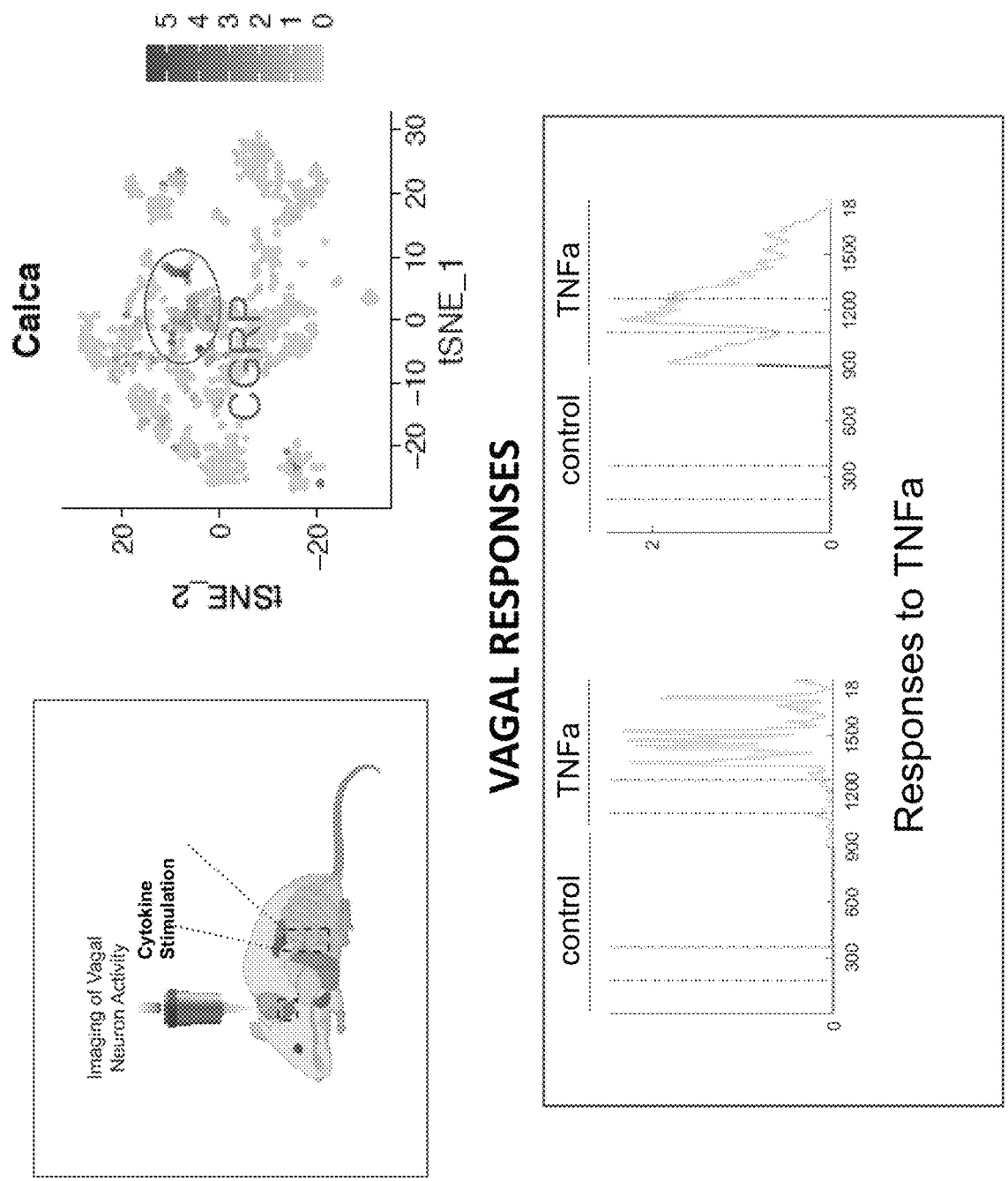
FIG. 23 shows the genetic identification of vagal neurons responding to pro-inflammatory signals. Single cell atlas of the vagal ganglia (Nodose), combined with functional imaging demonstrate that the Calca-expressing (calcitonin gene-related peptide-CGRP) neurons in the vagal ganglia carry TNFa pro-inflammatory signals from the body to the brain.
Figure 25:
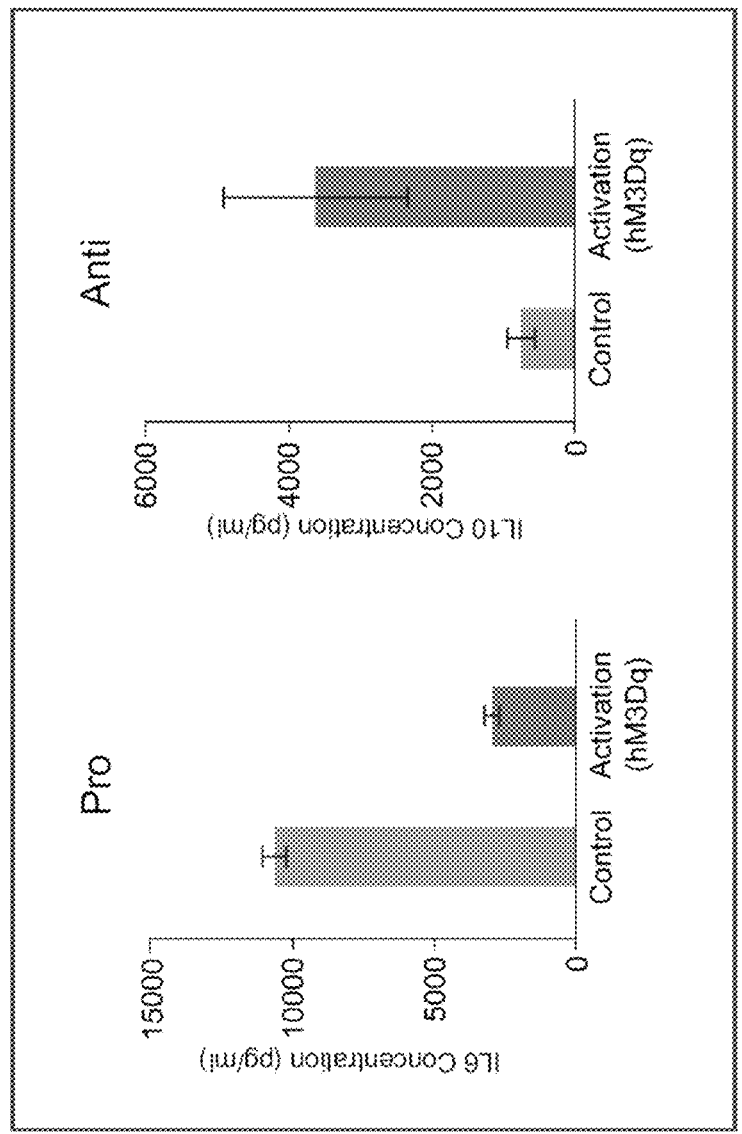
FIG. 25 shows that activating the cNST Crhr2 neurons is sufficient to suppress immune response/inflammation.

The single cell atlas of the vagal ganglia (Nodose) was used, combined with functional imaging to demonstrate that TrpA1-expressing Neuron in the vagal ganglia respond to anti-inflammatory signals (FIG. 21). Further, single cell atlas of the vagal ganglia (Nodose), combined with functional imaging demonstrate that the Calca-expressing (calcitonin gene-related peptide-CGRP) neurons in the vagal ganglia carry TNFa pro-inflammatory signals from the body to the brain (FIG. 23).

The TRPA1-expressing neuron in the vagal ganglia trigger the brain modulation of the immune response, and their artificial activation (chemogenetically in this example) mimic the effect of activating the cNST neurons, and lead to the suppression of pro-inflammatory cytokines, and the induction of anti-inflammatory ones (FIG. 22).

Immune responses are a critical point of physiological modulation in a wide range of treatments, diseases and disorders. The ability to bias immune responses (i.e., suppress or enhance) via neural circuits provides exciting novel therapeutic opportunities. The disclosed work provides a novel platform (i.e., imaging of nodose ganglion) to screen small molecules that can be administered peripherally to alter immune responses. The identification of genetically defined populations in the nodose provides candidates for pharmacologically targeted interventions. Interventions may also act centrally at the cNST by using an approach to target specifically the neurons identified in our studies that mediate top-down immune modulation.

FIG. 5. demonstrates that neurons in the caudal nucleus of the solitary tract are activated upon immune stimulation with the known immunostimulant LPS. This finding illustrates a direct neuronal response to immune system activation in a specific area of the brain. Importantly, FIG. 12. demonstrates this pathway is bidirectional and that direct stimulation of neurons in the caudal nucleus of the solitary tract suppresses secretion of the pro-inflammatory cytokine TNFa after LPS stimulation. Relatedly, following activation of the caudal nucleus of the solitary tract, the anti-inflammatory cytokine IL-10 is secreted in greater quantities after LPS stimulation. This establishes that activation of neurons in the caudal nucleus of the solitary tract is a novel method to regulate immune responses.

FIGS. 7-9. demonstrate that subsets of neurons in the nodose ganglion respond to either pro-inflammatory cytokines or anti-inflammatory cytokines through activation. These neuronal subsets can be used as a readout to assess the effect of different therapeutic agents on immune system activation. Using the GECI system described, immune system activation or suppression from a therapeutic agent can be determined via a florescence or luminescence readout from neurons that respond to either pro-inflammatory signals or neurons that respond to anti-inflammatory signals.

When ranges are used herein for physical properties, such as molecular weight, or chemical properties, such as chemical formulae, all combinations, and subcombinations of ranges for specific embodiments therein are intended to be included.

Those skilled in the art will appreciate that numerous changes and modifications can be made to the preferred embodiments of the methods and that such changes and modifications can be made without departing from the spirit of the methods. It is, therefore, intended that the appended claims cover all such equivalent variations as fall within the true spirit and scope of the methods.

What is claimed:

1. A method of assessing the ability of a therapeutic agent to regulate an immune response, comprising
administering the therapeutic agent to a subject;
measuring in the subject, in response to the therapeutic agent:
a) activation of nodose ganglion neurons which are activated by pro-inflammatory cytokines; and
b) activation of nodose ganglion neurons which are activated by anti-inflammatory cytokines; and
comparing the activation by the therapeutic agent of nodose ganglion neurons which are activated by pro-inflammatory cytokines to the activation by the therapeutic agent of nodose ganglion neurons which are activated by anti-inflammatory cytokines.

2. The method of claim 1, wherein the measuring activation comprises detecting calcium response.

3. The method of claim 2, wherein the nodose ganglion neurons comprise a calcium indicator.

4. The method of claim 3, wherein the calcium indicator is genetically encoded in the nodose ganglion neurons.

5. The method of claim 3, wherein the calcium indicator is a fluorescent or luminescent calcium indicator.

6. The method of claim 5, wherein the calcium indicator comprises GCaMP6s.

7. The method of claim 5, wherein detecting calcium response comprises in vivo imaging of the calcium indicator.

8. The method of claim 1, wherein the therapeutic agent is administered to the subject intraperitoneally, subcutaneously, or intravascularly.

9. The method of claim 1, wherein the therapeutic agent is a small molecule compound, an antibody, a protein, or a nucleic acid.

10. The method of claim 1, wherein the subject is a mammal.

11. The method of claim 1, wherein the subject is a mouse.

12. A method of assessing an alteration of an immune response in a subject, the method comprising:
administering a small molecule compound to the subject;
measuring in the subject, in response to the small molecule compound:
a) activation of a neuronal subset of nodose ganglion neurons activated by pro-inflammatory cytokines; and
b) activation of a neuronal subset of nodose ganglion neurons activated by anti-inflammatory cytokines; and
comparing the activation of the neuronal subset activated by pro-inflammatory cytokines to the activation of the neuronal subset activated by anti-inflammatory cytokines.

13. The method of claim 12, wherein measuring the activation of the neuronal subsets comprises detecting a signal in the neuronal subsets.

14. The method of claim 12, wherein the subject is a mammal.

15. The method of claim 12, wherein the subject is a mouse.

* * * * *